United States Patent [19]
Mitchell

[11] Patent Number: 6,013,487
[45] Date of Patent: *Jan. 11, 2000

[54] CHIMERIC RNA MOLECULES GENERATED BY TRANS-SPLICING

[76] Inventor: Lloyd G. Mitchell, c/o Intronn LLC 710 W. Main St., Durham, N.C. 27701

[*] Notice: This patent issued on a continued prosecution application filed under 37 CFR 1.53(d), and is subject to the twenty year patent term provisions of 35 U.S.C. 154(a)(2).

[21] Appl. No.: 08/766,354

[22] Filed: Dec. 13, 1996

Related U.S. Application Data

[60] Provisional application No. 60/008,717, Dec. 15, 1995.

[51] Int. Cl.[7] .............................. C07H 21/02; C12N 5/10; C12N 15/09; C12P 19/34
[52] U.S. Cl. ................. 435/91.3; 435/91.31; 435/320.1; 435/325; 435/455; 536/23.1
[58] Field of Search .................................. 435/91.1, 91.3, 435/91.31, 172.3, 325, 375, 419, 252.3, 254.11, 320.1; 514/44; 536/23.1, 24.5

[56] References Cited

U.S. PATENT DOCUMENTS

| | | | |
|---|---|---|---|
| 5,498,531 | 3/1996 | Jarrell | 435/91.31 |
| 5,641,673 | 6/1997 | Haseloff et al. | 435/325 |
| 5,667,969 | 9/1997 | Sullenger et al. | 435/6 |
| 5,863,774 | 1/1999 | Haseloff et al. | 435/172.3 |
| 5,866,384 | 2/1999 | Haseloff et al. | 800/285 |
| 5,874,414 | 2/1999 | Haseloff et al. | 514/44 |
| 5,882,907 | 3/1999 | Haseloff et al. | 435/172.3 |

FOREIGN PATENT DOCUMENTS

| | | |
|---|---|---|
| 92/13089 | 8/1992 | WIPO . |

OTHER PUBLICATIONS

Puttaraju et al. "Spliceosome–mediated RNA trans–splicing as a tool for gene therapy." Nature Biotechnology 17:246–252, 1999.

Crystal "Transfer of Genes to humans: Early lessons and obstacles to success" Science 270: 404410, Oct. 1995.

Christoffersen et al. "Ribozymes as human therapeutic agents" J. Med. Chem. 38(12): 2023–2037, Jun. 1995.

Stull et al. "Antigene, ribozyme and aptamer nucleic acid drugs: Progress and prospects" Pharm. Res. 12(4): 465–483, Apr. 1995.

"Report and recommendations of the panel to assess the NIH investment in research on gene therapy" Orkin and Motulsky, co–chairs. National Institutes of Health, Dec. 1995.

Linda Bonen, The FASEB Journal, (Jan. 1993), 40–46, "Trans–splicing of pre–mRNA in plants, animals, and protists", vol. 7.

Richard C. Mulligan, Science, (May 1993), 926–932, "The Basic Science of Gene Therapy", vol. 260.

E. Uhlmann and A. Peyman, Chemical Reviews (Jun. 1990), 543–584, "Antisense Oligonucleotides: A New Therapeutic Principle", vol. 90 No. 4.

(List continued on next page.)

*Primary Examiner*—Nancy Degen
*Assistant Examiner*—Thomas G. Larson
*Attorney, Agent, or Firm*—Baker & Botts; Rochelle K. Seide

[57] ABSTRACT

The molecules and methods of the present invention provide a means for in vivo production of a therapeutic molecule in a selected subset of cells. The pre-therapeutic molecules of the invention are substrates for a trans-splicing reaction between the pre-therapeutic molecules and a pre-mRNA which is uniquely expressed in the specific target cells. The in vivo trans-splicing reaction provides an active therapeutic RNA which is functional as RNA or encodes a protein to be expressed in the target cells. The expression product of the mRNA is a protein of therapeutic value to the cell or a toxin which causes killing of the specific cells.

34 Claims, 10 Drawing Sheets

OTHER PUBLICATIONS

Hajduk et al, The American Journal of the Medical Sciences, (Apr. 1992), 258–270, "Molecular Biology of African Trypanosomes: Developmentof New Strategies to Combat and Old Disease", vol. 303, No. 4.

Wittop–Koning and Schümperli, Eur. J. Biochem., (1994), "RNAs and ribonucleoproteins in recognition and catalysis", 219: 25–42.

Purcell and Martin, Journal of Virology, (Nov. 1993), 6365–6378, "Alternative Splicing of Human Immunodeficiency Virus Type 1 mRNA Modulates Viral Protein Expression, Replication, and Infectivity", vol. 67, No. 11.

J. Cohen and M. Hogan, Scientific American, (Dec. 1994), 76–82, "The New Genetic Medicines".

Masayori Inouye, Gene, (1988), 25–34, "Antisense RNA: its functions and applicaitons in gene regulation—a review", vol. 72.

Phillip A. Sharp, Cell, (Jul. 1987), 147–148, "Trans Splicing: Varation on a Familiar Theme?", vol. 50.

Harold M. Weintraub, Scientific American (Jan. 1990), 40–46, "Antisense RNA and DNA".

Gesteland and Atkins, Cell, (Jun. 1994), 801–802, "The RNA World: A Snapshot in Time", vol. 77.

Konarska, Padgett, and Sharp, Cell, (Aug. 1985), 165–171, "Trans Splicing of mRNA Precursors In Vitro", vol. 42.

Timothy W. Nilsen, Cell, (Jul. 1994), 1–4, "RNA—RNA Interactions in the Spliceosome: Unraveling the Ties That Bind", vol. 78.

Phillip A. Sharp, Cell, (Jun. 1994), 805–815, "Split Genes and RNA Splicing", vol. 77.

M. Vellard et al, Oncogene, (1991), 505–514, "C–myb proto–oncogene: evidence for intermolecular recombination of coding sequences", 6.

M. Vellard et al, Proc. Natl. Acad. Sci. USA, (Apr. 1992), 2511–2515, "A potential splicing factor is encoded by the opposite strand of the trans–spliced c–myb exon", vol. 89.

Eul, Graessmann and Graessmann, The EMBO Journal, (1995), 3226–3235, "Experimental evidence for RNA trans–splicing in mammalian cells". vol. 14, No. 13.

B. Sullenger and T. Cech, Nature, (Oct. 1994), 619–622, "Ribozyme–mediated repair of defective mRNA by targeted trans–splicing" vol. 371.

Pre-therapeutic RNA
FIG. 1A
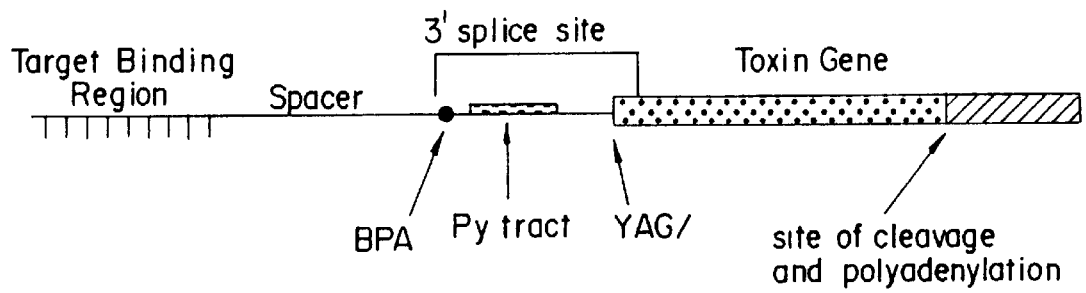
'SAFETY' REGION OF PTM COVERING BRANCH SITE AND PYRIMIDINE TRACK VIA WEAK HOMOLOGY
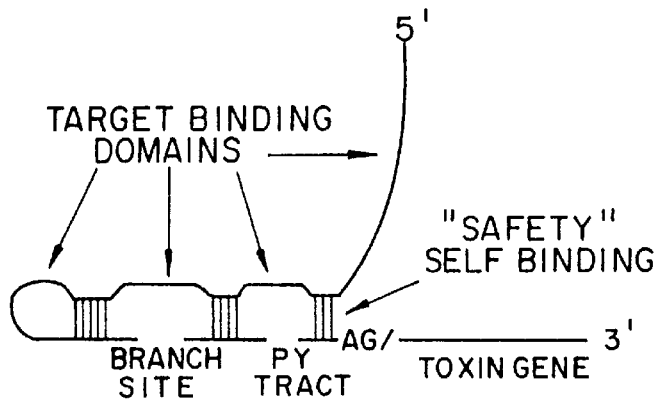
FIG. 1B
REMOVAL OF 'SAFETY' COVERING PTM 3' SPLICE-SITE BY BINDING TO TARGET PRE-mRNA
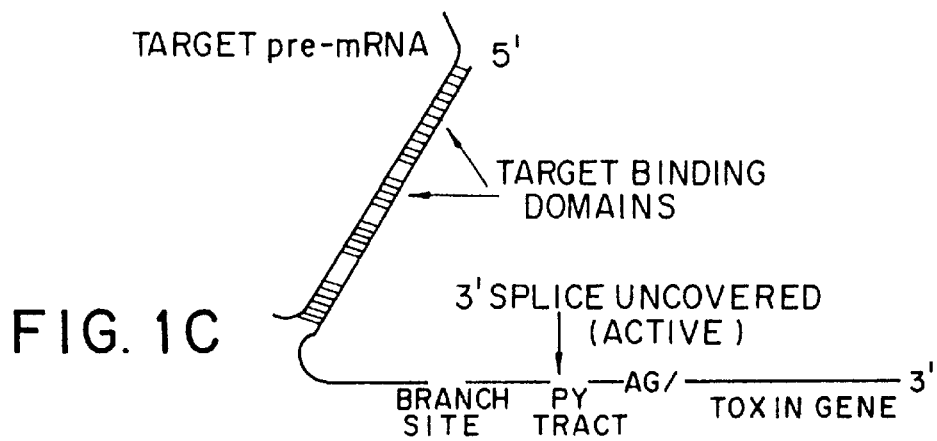
FIG. 1C

FIG. 2A

5' — Exon A — Intron — Exon B — 3'
A-B mRNA
↑ cis-splicing

FIG. 2B

Exon A 5' — Intron — Exon B 3'
Pre-therapeutic RNA

FIG. 2C

5' — A-Toxin mRNA — 3'

```
   1  ccggcgttgc gtatccagtg gctacactca ggttgtaatg attgggatga tgtacctgat
  61  ctgagagcga ttaaaaactc attgaggagt aggtcccgat tggttttgc tagtgaagct
 121  tagctagctt tccccatgta accaatctat caaaaaaggg cattgatttc agagcaccct
 181  tataattagg atagctttac ctaattattt tatgagtcct ggtaagggga tacgttgtga
 241  gcagaaaact gtttgcgtca atcttaatag gggcgctact ggggataggg gccccacctt
 301  cagcccatgc aggcgctgat gatgttgttg attcttctaa atcttttgtg atggaaaact
 361  tttcttcgta ccacgggact aaacctggtt atgtagattc cattcaaaaa ggtatacaaa
 421  agccaaaatc tggtacacaa ggaaattatg acgatgattg gaaagggttt tatagtaccg
 481  acaataaata cgacgctgcg ggatactctg tagataatga aaacccgctc tctggaaaag
 541  ctggaggcgt ggtcaaagtg acgtatccag gactgacgaa ggttctcgca ctaaaagtgg
 601  ataatgccga aactattaag aaagagttag gtttaagtct cactgaaccg ttgatggagc
 661  aagtcggaac ggaagagttt atcaaaaggt tcggtgatgg tgcttcgcgt gtagtgctca
 721  gccttccctt cgctgagggg agttctagcg ttgaatatat taataactgg gaacaggcga
 781  aagcgttaag cgtagaactt gagattaatt ttgaaacccg tggaaaacgt ggccaagatg
 841  cgatgtatga gtatatggct caagcctgtg caggaaatcg tgtcaggcga tcagtaggta
 901  gctcattgtc atgcataaat cttgattggg atgtcataag ggataaaact aagacaaaga
 961  tagagtcttt gaaagagcat ggccctatca aaaataaaat gagcgaaagt cccaataaaa
1021  cagtatctga ggaaaaagct aaacaatacc tagaagaatt tcatcaaacg gcattagagc
1081  atcctgaatt gtcagaactt aaaaccgtta ctgggaccaa tcctgtattc gctggggcta
1141  actatgcggc gtgggcagta acgttgcgc aagttatcga tagcgaaaca gctgataatt
1201  tggaaaagac aactgctgct ctttcgatac ttcctggtat cggtagcgta atgggcattg
1261  cagacggtgc cgttcaccac aatacagaag agatagtggc acaatcaata gctttatcgt
1321  ctttaatggt tgctcaagct attccattgg taggagagct agttgatatt ggtttcgctg
1381  catataattt tgtagagagt attatcaatt tatttcaagt agttcataat tcgtataatc
1441  gtcccgcgta ttctccgggg cataaaacgc aaccatttct tcatgacggg tatgctgtca
1501  gttggaacac tgttgaagat tcgataatcc gaactggttt tcaaggggag agtgggcacg
1561  acataaaaat tactgctgaa ataccccgc ttccaatcgc gggtgtccta ctaccgacta
1621  ttcctggaaa gctggacgtt aataagtcca agactcatat ttccgtaaat ggtcggaaaa
1681  taaggatgcg ttgcagagct atagacggtg atgtaacttt ttgtcgccct aaatctcctg
1741  tttatgttgg taatggtgtg catgcgaatc ttcacgtggc atttcacaga agcagctcgg
1801  agaaaattca ttctaatgaa atttcgtcgg attccatagg cgttcttggg taccagaaaa
1861  cagtagatca caccaaggtt aattctaagc tatcgctatt ttttgaaatc aaaagctgaa
1921  aggtagtggg gtcgtgtgcc gg
```

FIG. 3B

- Partial sequences of experimental pre-therapeutic molecules (PTM) showing TARGET BINDING REGION (complementary to β HCG intron 1, nucleotide 903-886), spacer region (in *italics*), branch point (branch point Adenosine in larger font), pyrimidine tract (Py), and 3' splice site ( AG/ ). The sequence (/GGCGCT . . . . . ) represents the entire coding sequence of diphtheria toxin subunit A. Sequences of the mutant constructs in which pyrimidine tract, 3' splice site AG was deleted, and stop codons inserted are also shown.

(1) PTM + : Has complementary binding domain to the intron 1 branch point of β HCG

```
   | Eco RI |  Xba I |   | Binding Domain  |      Branch Pt
5' GAATTCTCTAGATGCTTCACCCGGGCCTGACTCGAGTACTAACTGGTACCTC
```

```
   pyrimidine tract  3' splice site/ diphtheria toxin subunit A
TTCTTTTTTTTCCTGCAG/GGCGCT . . . . . . . . . . . . . . .
```

(2) PTM + spacer: Has 30 nt spacer between complementary binding domain and the branch point

```
   Eco RI  |  Xba I |   | Binding Domain  |    Spacer   Region
5' GAATTCTCTAGATGCTTCACCCGGGCCTGACTCGAGAACATTATTATAACGTTGC
```

```
     Branch Pt                   pyrimidine tract
TCGAGTACTAACTGGTACCTCTTCTTTTTTTTCCTGCAG/GGCGCT . . . .
```

(3) PTM - : Has weak complementarity to β HCG intron 1 branch point

5' GAATTCTCTAGATCAGGCCCGGGTGAAGCACTCGAGTACTAACTGGTACCTC

TTCTTTTTTTTCCTGCAG/GGCGCT . . . . . .

(4) "No Stick" PTM, TB with spacer: No complementarity to β HCG intron 1

5' GAATTCTCTAGACAACGTTAATAATAATGTT*CTCGAGAACATTATTATAACG*

*TTGCTCGAG*TACTAACTGGTACCTCTTCTTTTTTTTCCTGCAG/GGCGCT . . . .

FIG.4A (5) PTM + Py tract (-) AG (-) mutant : Identical to (2), except splice acceptor any pyrimidine tract is mutated to eliminate 3' splice site functionality

5' GAATTCTCTAGATGCTTCACCCGGGCCTGACTCGAGAACATTATTATAACGTTGC

TCGAGTACTAACTGGTACCCGAACTGGACGCGGTTAACG/GGCGCT.....
             Mutated Pyrimidine tract, No AG (6) PTM + Py tract (-) AG (-) mutant with stop codons: Same as (5), except that the mutated pyrimidine tract (CCGTGATAATAGCGGTTAAC) contains 3 in frame stop codons (TGA, TAA, TAG)

5' GAATTCTCTAGATGCTTCACCCGGGCCTGACTCGAGAACATTATTATAACGTTGC

TCGAGTACTAACTGGTACCCGTGATAATAGCGGTTAACG/GGCGCT.....
            Mutated Pyrimidine tract, No AG (7) PTM + AG (-) mutant: Same as (2) except that 3' splice acceptor AG is deleted (↑)

5' GAATTCTCTAGATGCTTCACCCGGGCCTGACTCGAGAACATTATTATAACGTTGC

TCGAGTACTAACTGGTACCTCTTCTTTTTTTTCCG/GGCGCT.....
                                      ↑

FIG.4B

HUMAN CHORIONIC GONADOTROPIN (HCG) GENE 6 BETA SUBUNIT

ORIGIN

```
   1  aagggagagg tggggctcgg gctgaatccc tcgttggggg gcatctgggt caagtggctt
  61  ccctggcagc acagtcacgg ggagaccctc tctcactggg cagaagctaa gtccgaagcc
 121  gcgcccctcc tgttaggttg gactgtggtg caggaaaggc tcaagtagag gagagttgag
 181  gcttcagtcc agcactttcc tcgggtcacg gcctcctcct ggttcccaag accccaccat
 241  aggcagaggc aggccttcct cacccctact ctctgtgcct ccagcctcga ctagtcccta
 301  acactcgacg actgagtctc agaggtcact tcaccgtggt ctccgcctca tccttggcgc
 361  tagaccactg aggggagagg actggggtgc tccgctgagc cactcctgtg cctccctggc
 421  cttgtctact tctcgccccc gaagggttag tgtcgagctc actccagcat cctacaacct
 481  cctggtggcc ttgccgcccc cacaacccctg aggtatgaag ccaggtacac caggcagggg
 541  acgcaccaag gatggagatg ttccaggtaa gactgcaggg cccctgggca ccttccacct
 601  ccttccaggc aatcactggc atgagaaggg gcagaccagt gtgagctgtg gaaggacgcc
 661  tctttctgga ggagtgtgac ccccagtaag cttcacgtgg ggcagttcct gagggtgggg
 721  atctgaaatg ttggggtatc tcaggtccct cgggctgtgg ggtgggctct gaaaggcagg
 781  tgtccgggtg gtgggtcctg aataggagat gccgggaagg gtctctgggt ctttgtgggt
 841  ggtgtaccct ggggatggg aaggccgggg ctcagggctg tggtctcagg cccgggtgaa
 901  gcagtgtcct tgtcccaggg gctgctgctg ttgctgctgc tgagcatggg cgggacatgg
 961  gcatccaagg agccacttcg gccacggtgc cgccccatca atgccaccct ggctgtggag
1021  aaggagggct gccccgtgtg catcaccgtc aacaccacca tctgtgccgg ctactgcccc
1081  accatggtga gctgcccggg gcccgggcag gtgctgccac ctcagggcca gacccacaga
1141  ggcagcgggg gaggaagggt ggtctgcctc tctggtcagg ggctgcggaa tggggtgtgg
1201  gagggcagga acagagggct tcctggaccc ctgagtctga gacctgtggg ggcagctggg
1261  gagctcagct gaggcgctgg cccaggcaca tgctcattcc cccactcaca cggcttccag
1321  acccgcgtgc tgcaggggt cctgccggcc ctgcctcagg tggtgtgcaa ctaccgcgat
1381  gtgcgcttcg agtccatccg gctccctggc tgcccgcgcg gcgtgaaccc cgtggtctcc
1441  tacgccgtgg ctctcagctg tcaatgtgca ctctgccgcc gcagcaccac tgactgcggg
1501  ggtcccaagg accaccccctt gacctgtgat gaccccgct tccaggcctc ctcttcctca
1561  aaggcccctc cccccagcct tccaagtcca tcccgactcc cggggccctc ggacaccccg
1621  atcctcccac aataaaggct tctcaatccg cactctggcg gtgtc
```

FIG.5B

Exon 1 of β HCG          566

5 - CAGGGGACGCACCAAGGATGGAGATGTTCCAGGGCGCTGATGATGTTGTTGATT
                                    ↑ 1st Coding Nucleotide of DTA

CTTCTAAATCTTTTGTGATGGAAAACTTTTCTTCGTACCACGGGACTAAACCTGGTTAT

GTAGATTCCATTCAAAAA -3

---

Sequence from gel (This is reversed due to the use of a reverse sequencing primer)

Diphtheria toxin subunit A >
TTTTGAATGGAATCTACATAACCAGGTTTAGTCCCGTGGTACGAAGAAAAGTTTTCC ATCACAAAAGATTTAGAAGAATCAACAACATCATCAGCGCCCTGGAACATCTCCAT
                                               ↑ beta HCG exon1
CCTTGGTGCGTCCCCTG - 3'

FIG.6B

SEQUENCE LISTING (1) GENERAL INFORMATION:

(iii) NUMBER OF SEQUENCES: 33

(2) INFORMATION FOR SEQ ID NO:1:

```
    (i) SEQUENCE CHARACTERISTICS:
         (A) LENGTH: 208 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:1:

GGGCGAATTC GAGCTCACTC TCTTCCGCAT CGCTGTCTGC GAGGTACCTG TTGGGGTGAG      60

TAGGATCCCT CTAAAAGCGG GCATGACTTC TAGAGTAGTC CAGGGTTTCC GAGGGTTTCC     120

GTCGACGATG TCATACTTAT CCTGGGCCCT TTTTTTTCCA CAGCTCGCGC TGCAGGACAA     180

ACTCTTCGCG GTCTTTGCAT GCAAGCTT                                        208

(2) INFORMATION FOR SEQ ID NO:2:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:2:

CATACTTATC CTGGGCCCTT TT                                               22

(2) INFORMATION FOR SEQ ID NO:3:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:3:

TTTTCCCGGG TCCTATTCAT AC                                               22

(2) INFORMATION FOR SEQ ID NO:4:

(i) SEQUENCE CHARACTERISTICS:
         (A) LENGTH: 258 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:4:

AAAAGGGCCC AGGATAAGTA TGCACGGCGA CTATTGATTC TGAGAACTGT GTTATACTAA      60

CGGAACTTCC CTTTTTTTTC CACAGAGCCA GCCAGAACTC GCCCCGGAAG ACCCCGAGGA     120

TGTCGAGCAC CACCACCACC ACCACTGAGA TCCGGCTGCT AACAAAGCCC GAAAGGAAGC     180

TGAGTTGGCT GCTGCCACGC TGAGCAATAA CTAGCATAAC CCCTTGGGGC CTCTAAACGG     240

GTCTTGAGGG GTTTTTTG                                                    258

(2) INFORMATION FOR SEQ ID NO:5:

(i) SEQUENCE CHARACTERISTICS:
         (A) LENGTH: 1942 base pairs
         (B) TYPE: nucleic acid
         (C) STRANDEDNESS: single
         (D) TOPOLOGY: linear
```

(ii) MOLECULE TYPE: DNA (xi) SEQUENCE DESCRIPTION: SEQ ID NO:5:

```
CCGGCGTTGC GTATCCAGTG GCTACACTCA GGTTGTAATG ATTGGGATGA TGTACCTGAT      60
CTGAGAGCGA TTAAAAACTC ATTGAGGAGT AGGTCCCGAT TGGTTTTTGC TAGTGAAGCT     120
TAGCTAGCTT TCCCCATGTA ACCAATCTAT CAAAAAAGGG CATTGATTTC AGAGCACCCT     180
TATAATTAGG ATAGCTTTAC CTAATTATTT TATGAGTCCT GGTAAGGGGA TACGTTGTGA     240
GCAGAAAACT GTTTGCGTCA ATCTTAATAG GGGCGCTACT GGGGATAGGG GCCCCACCTT     300
CAGCCCATGC AGGCGCTGAT GATGTTGTTG ATTCTTCTAA ATCTTTTGTG ATGGAAAACT     360
TTTCTTCGTA CCACGGGACT AAACCTGGTT ATGTAGATTC CATTCAAAAA GGTATACAAA     420
AGCCAAAATC TGGTACACAA GGAAATTATG ACGATGATTG GAAAGGGTTT TATAGTACCG     480
ACAATAAATA CGACGCTGCG GGATACTCTG TAGATAATGA AAACCCGCTC TCTGGAAAAG     540
CTGGAGGCGT GGTCAAAGTG ACGTATCCAG GACTGACGAA GGTTCTCGCA CTAAAAGTGG     600
ATAATGCCGA AACTATTAAG AAAGAGTTAG GTTTAAGTCT CACTGAACCG TTGATGGAGC     660
AAGTCGGAAC GGAAGAGTTT ATCAAAAGGT TCGGTGATGG TGCTTCGCGT GTAGTGCTCA     720
GCCTTCCCTT CGCTGAGGGG AGTTCTAGCG TTGAATATAT TAATAACTGG GAACAGGCGA     780
AAGCGTTAAG CGTAGAACTT GAGATTAATT TTGAAACCCG TGGAAAACGT GGCCAAGATG     840
CGATGTATGA GTATATGGCT CAAGCCTGTG CAGGAAATCG TGTCAGGCGA TCAGTAGGTA     900
GCTCATTGTC ATGCATAAAT CTTGATTGGG ATGTCATAAG GATAAAACT AAGACAAAGA     960
TAGAGTCTTT GAAAGAGCAT GGCCCTATCA AAATAAAAT GAGCGAAAGT CCCAATAAAA    1020
CAGTATCTGA GGAAAAAGCT AAACAATACC TAGAAGAATT TCATCAAACG GCATTAGAGC    1080
ATCCTGAATT GTCAGAACTT AAAACCGTTA CTGGGACCAA TCCTGTATTC GCTGGGGCTA    1140
ACTATGCGGC GTGGGCAGTA AACGTTGCGC AAGTTATCGA TAGCGAAACA GCTGATAATT    1200
TGGAAAAGAC AACTGCTGCT CTTTCGATAC TTCCTGGTAT CGGTAGCGTA ATGGGCATTG    1260
CAGACGGTGC CGTTCACCAC AATACAGAAG AGATAGTGGC ACAATCAATA GCTTTATCGT    1320
CTTTAATGGT TGCTCAAGCT ATTCCATTGG TAGGAGAGCT AGTTGATATT GGTTTCGCTG    1380
CATATAATTT TGTAGAGAGT ATTATCAATT TATTTCAAGT AGTTCATAAT TCGTATAATC    1440
GTCCCGCGTA TTCTCCGGGG CATAAAACGC AACCATTTCT TCATGACGGG TATGCTGTCA    1500
GTTGGAACAC TGTTGAAGAT TCGATAATCC GAACTGGTTT TCAAGGGGAG AGTGGGCACG    1560
ACATAAAAAT TACTGCTGAA ATACCCCGC TTCCAATCGC GGGTGTCCTA CTACCGACTA    1620
TTCCTGGAAA GCTGGACGTT AATAAGTCCA AGACTCTATAT TTCCGTAAAT GGTCGGAAAA    1680
TAAGGATGCG TTGCAGAGCT ATAGACGGTG ATGTAACTTT TTGTCGCCCT AAATCTCCTG    1740
TTTATGTTGG TAATGGTGTG CATGCGAATC TTCACGTGGC ATTTCACAGA AGCAGCTCGG    1800
AGAAAATTCA TTCTAATGAA ATTTCGTCGG ATTCCATAGG CGTTCTTGGG TACCAGAAAA    1860
CAGTAGATCA CACCAAGGTT AATTCTAAGC TATCGCTATT TTTTGAAATC AAAAGCTGAA    1920
AGGTAGTGGG GTCGTGTGCC GG                                            1942
```

(2) INFORMATION FOR SEQ ID NO:6:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:6:

GAATTCTCTA GATGCTTCAC CCGGGCCTGA CTCGAGTACT AACTGGTACC TCTTCTTTTT     60

TTTCCTGCAG GGCGCT     76

(2) INFORMATION FOR SEQ ID NO:7:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GAATTCTCTA GATGCTTCAC CCGGGCCTGA CTCGAGAACA TTATTATAAC GTTGCAGTAC     60

TAACTGGTAC CTCTTCTTTT TTTTCCTGCA GGGCGCT     97

(2) INFORMATION FOR SEQ ID NO:8:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GAATTCTCTA GATCAGGCCC GGGTGAAGCA CTCGAGTACT AACTGGTACC TCTTCTTTTT     60

TTTCCTGCAG GGCGCT     76

(2) INFORMATION FOR SEQ ID NO:9:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GAATTCTCTA GACAACGTTA ATAATAATGT TCTCGAGAAC ATTATTATAA CGTTGCTCGA     60

GTACTAACTG GTACCTCTTC TTTTTTTTCC TGCAGGGCGC T     101

(2) INFORMATION FOR SEQ ID NO:10:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GAATTCTCTA GATGCTTCAC CCGGGCCTGA CTCGAGAACA TTATTATAAC GTTGCTCGAG     60

TACTAACTGG TACCCGAACT GGACGCGGTT AACGGGCGCT     100

(2) INFORMATION FOR SEQ ID NO:11:

(i) SEQUENCE CHARACTERISTICS:
        (A) LENGTH: 100 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GAATTCTCTA GATGCTTCAC CCGGGCCTGA CTCGAGAACA TTATTATAAC GTTGCTCGAG      60

TACTAACTGG TACCCGTGAT AATAGCGGTT AACGGGCGCT                           100

(2) INFORMATION FOR SEQ ID NO:12:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GAATTCTCTA GATGCTTCAC CCGGGCCTGA CTCGAGAACA TTATTATAAC GTTGCTCGAG      60

TACTAACTGG TACCTCTTCT TTTTTTTCCG GGCGCT                                96

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGCGCTGCAG GGCGCTGATG ATGTTGTTG                                        29

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GGCGAAGCTT GGATCCGACA CGATTTCCTG CACAGG                                36

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGAAAAAAAA GAAGAGGTAC CAGTTAGTAC TCGAGTCAGG CCCGGGTGAA GCATCTAGAG      60

(2) INFORMATION FOR SEQ ID NO:16:

(i) SEQUENCE CHARACTERISTICS:
        (A) LENGTH: 68 base pairs
        (B) TYPE: nucleic acid
```

```
        (C) STRANDEDNESS: single
        (D) TOPOLOGY: linear (ii) MOLECULE TYPE: DNA (xi) SEQUENCE DESCRIPTION: SEQ ID NO:16:

AATTCTCTAG ATGCTTCACC CGGGCCTGAC TCGAGTACTA ACTGGTACCT CTTCTTTTTT      60

TTCCTGCA                                                              68

(2) INFORMATION FOR SEQ ID NO:17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

AATTCTCTAG ATCAGGCCCG GGTGAAGCAC TCGAG                                 35

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TGCTTCACCC GGGCCTGATC TAGAG                                            25

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TCGAGCAACG TTATAATAAT GTTC                                             24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TCGAGAACAT TATTATAACG TTGC                                             24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:21:

CTAGACAACG TTATAATAAT GTTC                                                24

(2) INFORMATION FOR SEQ ID NO:22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:22:

TCGAGAACAT TATTATAACG TTGT                                                24

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

CCGAACTGGA CGCGGTTAAC                                                     20

(2) INFORMATION FOR SEQ ID NO:24:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

GTTAACCGCG TCCAGTTCGG GTAC                                                24

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

CCGTGATAAT AGCGGTTAAC                                                     20

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

GTTAACCGCT ATTATCACGG GTAC                                                24

(2) INFORMATION FOR SEQ ID NO:27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
ACTGGTACCT CTTCTTTTTT TTCCTGCGGC GCTG                                    34
```

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
GGCGAAGCTT GGATCCGACA CGATTTCCTG CACAGG                                  36
```

(2) INFORMATION FOR SEQ ID NO:29:

(i) SEQUENCE CHARACTERISTICS:
        (A) LENGTH: 1665 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
AAGGGAGAGG TGGGGCTCGG GCTGAATCCC TCGTTGGGGG GCATCTGGGT CAAGTGGCTT          60
CCCTGGCAGC ACAGTCACGG GGAGACCCTC TCTCACTGGG CAGAAGCTAA GTCCGAAGCC         120
GCGCCCCTCC TGTTAGGTTG GACTGTGGTG CAGGAAAGGC TCAAGTAGAG GAGAGTTGAG         180
GCTTCAGTCC AGCACTTTCC TCGGGTCACG GCCTCCTCCT GGTTCCCAAG ACCCCACCAT         240
AGGCAGAGGC AGGCCTTCCT ACACCCTACT CTCTGTGCCT CCAGCCTCGA CTAGTCCCTA         300
ACACTCGACG ACTGAGTCTC AGAGGTCACT TCACCGTGGT CTCCGCCTCA TCCTTGGCGC         360
TAGACCACTG AGGGGAGAGG ACTGGGGTGC TCCGCTGAGC CACTCCTGTG CCTCCCTGGC         420
CTTGTCTACT TCTCGCCCCC GAAGGGTTAG TGTCGAGCTC ACTCCAGCAT CCTACAACCT         480
CCTGGTGGCC TTGCCGCCCC CACAACCCCG AGGTATGAAG CCAGGTACAC CAGGCAGGGG         540
ACGCACCAAG GATGGAGATG TTCCAGGTAA GACTGCAGGG CCCCTGGGCA CCTTCCACCT         600
CCTTCCAGGC AATCACTGGC ATGAGAAGGG GCAGACCAGT GTGAGCTGTG GAAGGACGCC         660
TCTTTCTGGA GGAGTGTGAC CCCCAGTAAG CTTCACGTGG GGCAGTTCCT GAGGGTGGGG         720
ATCTGAAATG TTGGGGTATC TCAGGTCCCT CGGGCTGTGG GGTGGGCTCT GAAAGGCAGG         780
TGTCCGGGTG GTGGGTCCTG AATAGGAGAT GCCGGGAAGG GTCTCTGGGT CTTTGTGGGT         840
GGTGTACCCT GGGGGATGGG AAGGCCGGGG CTCAGGGCTG TGGTCTCAGG CCCGGGTGAA         900
GCAGTGTCCT TGTCCCAGGG GCTGCTGCTG TTGCTGCTGC TGAGCATGGG CGGGACATGG         960
GCATCCAAGG AGCCACTTCG GCCACGGTGC CGCCCCATCA ATGCCACCCT GGCTGTGGAG        1020
AAGGAGGGCT GCCCCGTGTG CATCACCGTC AACACCACCA TCTGTGCCGG CTACTGCCCC        1080
```

```
ACCATGGTGA GCTGCCCGGG GCCCGGGCAG GTGCTGCCAC CTCAGGGCCA GACCCACAGA      1140

GGCAGCGGGG GAGGAAGGGT GGTCTGCCTC TCTGGTCAGG GGCTGCGGAA TGGGGTGTGG      1200

GAGGGCAGGA ACAGAGGGCT TCCTGGACCC CTGAGTCTGA GACCTGTGGG GGCAGCTGGG      1260

GAGCTCAGCT GAGGCGCTGG CCCAGGCACA TGCTCATTCC CCCACTCACA CGGCTTCCAG      1320

ACCCGCGTGC TGCAGGGGGT CCTGCCGGCC CTGCCTCAGG TGGTGTGCAA CTACCGCGAT      1380

GTGCGCTTCG AGTCCATCCG GCTCCCTGGC TGCCCGCGCG GCGTGAACCC CGTGGTCTCC      1440

TACGCCGTGG CTCTCAGCTG TCAATGTGCA CTCTGCCGCC GCAGCACCAC TGACTGCGGG      1500

GGTCCCAAGG ACCACCCCTT GACCTGTGAT GACCCCCGCT TCCAGGCCTC CTCTTCCTCA      1560

AAGGCCCCTC CCCCCAGCCT TCCAAGTCCA TCCCGACTCC CGGGGCCCTC GGACACCCCG      1620

ATCCTCCCAC AATAAAGGCT TCTCAATCCG CACTCTGGCG GTGTC                     1665
```

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
CATCGTCATA ATTTCCTTGT G                                                 21
```

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

```
ACCGGAATTC ATGAAGCCAG GTACACCAGG                                        30
```

(2) INFORMATION FOR SEQ ID NO:32:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

```
CAGGGGACGC ACCAAGGATG GAGATGTTCC AGGGCGCTGA TGATGTTGTT GATTCTTCTA        60

AATCTTTTGT GATGGAAAAC TTTTCTTCGT ACCACGGGAC TAAACCTGGT TATGTAGATT       120

CCATTCAAAA A                                                           131
```

(2) INFORMATION FOR SEQ ID NO:33:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TTTTGAATGG AATCTACATA ACCAGGTTTA GTCCCGTGGT ACGAAGAAAA GTTTTCCATC    60

ACAAAAGATT TAGAAGAATC AACAACATCA TCAGCGCCCT GGAACATCTC CATCCTTGGT   120

GCGTCCCCTG                                                          130

CHIMERIC RNA MOLECULES GENERATED BY TRANS-SPLICING

This application, claims the benefit of U.S. Provisional Application Ser. No. 60/008,717, filed Dec. 15, 1955.

BACKGROUND OF THE INVENTION

1. Field of the Invention

The molecules and methods of the present invention provide a means for expressing a heterologous gene in a selected subset of cells. The precursor-therapeutic molecules (PTM) of the invention are substrates for a targeted or defined trans-splicing reaction between the precursor therapeutic molecules and pre-mRNA molecules which are uniquely expressed in the specific target cells. The PTMs may be RNA, DNA, or other molecules such as peptide nucleic acids (PNA). The in vivo trans-splicing reaction provides an active therapeutic molecule which may be expressed in the target cells. The expression product of the mRNA may be a protein of therapeutic value to the cell, or a toxin which kills the specific cells. Alternatively, the therapeutic RNA (th-RNA) or other molecule may itself perform a therapeutic function. On another embodiment of the invention multiple PTMs may be used in combination to achieve a therapeutic effect.

2. Description of Related Art

One of the greatest challenges in the therapy of many life-threatening disease conditions, such as cancer and AIDS, is the administration of a therapeutic molecule to the specific target cells without administering the same molecule to other cells in the organism. Previous efforts to solve this problem have included gene therapy with viral vectors, delivery of drugs or toxins conjugated to monoclonal antibodies, and others. To date, these methods have not been entirely effective.

The method of the present invention does not require delivery to only the targeted cells. The precursor molecule to the therapeutic molecule can be delivered to all cells in the organism, and may be taken up by all cells in the organism, but the therapeutic mRNA is only created in vivo in the specific target cells. The specificity of this therapy relies on the unique (restricted) transcription of the target pre-mRNA in the target cells. The normal cells (non-targeted) will not transcribe (or transcribe only minimally) the target gene. Therefore, selective creation of the therapeutic molecule will not take place in such normal cells (or will only take place to a very minimal extent).

One important way that eucaryotic cells in the same organism differ from one another, despite virtual identity of gene content, is that they express different genes or portions of those genes. This regulation of gene expression operates at many levels; classical studies on gene expression demonstrate control at the level of transcription and translation. More recent work indicates that cells also have the ability to regulate gene expression by gene copy number and regulation of splicing.

The genes, stored as DNA sequences in the chromosome, are transcribed into pre-mRNAs which contain coding regions (exons) and generally also contain intervening noncoding regions (introns). The pre-mRNA is processed in the nucleus, removing the introns, along with any unwanted exons. The remaining exons are spliced together, forming an mRNA, which is exported from the nucleus to the cytoplasm for translation into a protein by the ribosomes. See, for example, Moore, M. J., C. C. Query, and P. A. Sharp, Cell, 77:805–815 (1994); Moore, M. J., C. C. Query, and P. A. Sharp, The RNA World, Cold Spring Harbor Laboratory Press, 303–358, (1993).

Introns are removed from pre-mRNAs in a precise process called splicing. Chow, L. T., R. E. Gelinas, T. R. Broker, R. J. Roberts, (1977) Cell, 12, 1–8; and Berget, S. M., C. Moore and P. A. Sharp (1977) Proc. Natl. Acad. Sci. USA 74, 3171–3175. Pre-mRNA splicing proceeds by a two-step mechanism. In the first step, the 5' splice site is cleaved, resulting in a "free" 5' exon and a lariat intermediate. (Moore, M. J. and P. A. Sharp, Nature, 365:364–368, 1993) The 5' nucleotide of the intron (usually guanine) forms the lariat intermediate through a 2',5'-phosphodiester link with the branch point nucleotide (usually adenosine) in the intron. In the second step, the 5' exon is ligated to the 3' exon with release of the intron as the lariat product. These steps are catalyzed in a complex of small nuclear ribonucleoproteins and proteins called the spliceosome (Moore et al., The RNA World).

The trans-esterification splicing reaction sites are defined by consensus sequences around the 5' and 3' splice sites. The 5' splice site consensus sequence is AG/GURAGU (where N=any nucleotide, A=adenosine, U=uracil, G=guanine, C=cytosine, R=purine, Y=pyrimidine, and /=the splice site). Moore et al., The RNA World. The underlined nucleotides are common to almost all pre-mRNA introns, with GC substituted in place of GU being a rare exception. The 3' splice site consists of three separate sequence elements: the branch point or branch site, a polypyrimidine tract and the 3' consensus sequence. These elements loosely define a 3' splice site region, which may encompass 100 nucleotides of the intron upstream of the 3' splice site. The branch point consensus sequence in mammals is YNCUGAC. The underlined A is the site of branch formation (the BPA=branch point adenosine). The 3' splice consensus sequence is YAG/G. Between the branch point and the splice site there is usually found a polypyrimidine tract, which is important in mammalian systems for efficient branch point utilization and 3' splice site recognition (Roscigno, R., M. Weiner and M. A. Garcia-Blanco, J. Biol. Chem. 268, 14, 11222–11229, 1993). The first YAG dinucleotide downstream from the branch point and polypyrimidine tract is the most commonly used 3' splice site. Smith, C. W. J., E. B. Porro, J. G. Patton and B. Nadal-Ginand (1989) Nature 342, 243–247.

Cis vs. trans-splicing

Usually exons are ligated to other exons in the same pre-mRNA, cis-splicing, and not to exons in other pre-mRNAs, trans-splicing. It is possible, however, to observe efficient trans-splicing in vitro by tethering two halves of a pre-mRNA using complementary sequences. These form stable double stranded stems by "Watson-Crick"-like base pairing. Konarska, M. M., R. A. Padgett and P. A. Sharp (1985), Cell 42, 165–171. This type of trans-splicing has not been clearly observed in vivo.

The mechanism of splice site approximation "through space" is independent of the intron between the splice sites for example in the trans-splicing observed commonly in trypanosomes and nematodes. Sutton, R. E. and J. C. Boothroyd, Cell 47, 527–535 (1986); Murphy, W. J. et al., Cell 47, 517–525 (1986); Krause, M. and D. Hirsh, Cell 49, 753–761 (1987). In these very special cases, the 5' splice site containing short leader (SL) RNA forms a small nuclear ribonucleoprotein particle (snRNP) that interacts with the 3' end of the intron in the larger pre-mRNA (Bruzik, J. P. and J. A. Steitz, Cell 62, 889–899 (1990); Bruzik, J. P. and T. Maniatis, Nature 360, 692–695 (1992). This type of splicing has not been observed to occur naturally in mammalian cells.

Konarska et al. (1985), D. Solnik (1985) Cell 42, 157–164 detected trans-splicing in vitro using RNAs that did not resemble the SL RNAs. RNA-RNA secondary structures which tethered the precursors significantly increased the efficiency of the trans-splicing reaction (from <1% to 15–30% of wild type cis-splicing efficiency).

Complementary RNA or DNA sequences can specifically base pair with unique target sequences of RNA or DNA. The specificity of binding is influenced by the sequence, the length of the complementary region, and any secondary structure at the binding site. In order to obtain binding specificity, a unique sequence is chosen as the target. A chain length of 17 nucleotides has been calculated to be sufficient to achieve binding specificity, that is, the statistical single occurrence of a unique polynucleotide target in the human haploid genome of $3 \times 10^9$ base pairs. M. Smith, Methods of DNA and RNA Sequencing, ed S. M. Weissman, Praeger, New York, N.Y., USA, p. 39 (1983). Duplex stability is independent of length for complementary sequences longer than 200 nucleotides [Steiner, R. F. and Beers, R. J. Jr. (1986)]. In Polynucleotides, (Elsevier, Amsterdam). Longer complementary sequences increase the stability of the duplex, but very long regions can interact with multiple mRNAs through base pairing involving only 510 contiguous bases, thus lowering their specificity. Complementary sequences may have non-binding RNA or DNA sequences or other nucleic acid analogs or chemical groups on either of their 5' and/or 3' ends. Binding may also be achieved through other mechanisms, for example triple helix formation, and protein-nucleic acid interactions, such as those between gene promoters and DNA. Examples of tissue specific promoters include the immunoglobulin promoter described by Brinster at. al., Nature, 306:332–336 (1983) and the insulin promoter described by Bucchini et. al., PNAS, 83:2511–2515 (1986). Other means of binding may be used which are known to those skilled in the art.

Toxins such as diphtheria toxin (DT), ricin, Pseudomonas toxin, shiga toxin, and cholera toxin are extremely potent. A single molecule of DT can kill a cell by acting enzymatically within the cytosol. Yamaizumi, M., E. Mekada, T. Uchida and Y. Okada, Cell 15, 245–250 (1978). These toxins appear to have a similar basic structure, consisting of an A and B subunit, wherein the B subunit binds to the cell surface and facilitates the translocation of the A subunit into the cell, and the A subunit possesses the enzymatic toxin activity. Collier, R. and J. Kondel, Biol. Chem. 246, 1496–1503 (1971); and Gill, D. and A. Pappenheimer, J. Biol. Chem. 246, 1492–1495 (1971). The DT A subunit (DT-A) catalyzes the transfer of ADP-ribose from NAD to an unusual amino acid (dipthamide) in elongation factor 2. Honjo, T., Y. Nishizuka and 0. Hayaishi, J. Biol. Chem. 243, 3553–3555 (1968); and Gill, D., A. Pappenheimer, R. Brown and J. Kurnick, J. of Experimental Medicine 129, 1–21 (1969). Such binding stops protein synthesis in the cell and is lethal to that cell. There are a number of therapeutic strategies which attempt to deliver or express the DT-A within selected cells, including transcriptionally regulating DT-A gene expression. (Robinson, D. F., T. H. Maxwell, Hum. Gene Ther., 6(2), 137–145, 1995; Cook D. R. et al., Cancer Biother., 9(2), 131–141, 1994; Curiel, T. J. et al., Hum. Gene Ther., 4(6), 741–747, 1993).

SUMMARY OF THE INVENTION

The present invention provides a novel method for the controlled expression of a heterologous gene product in a desired target cell by creating a unique th-mRNA through a trans-splicing mechanism. The unique mRNA has one of the following functions; it codes for a protein which has a therapeutic effect, it selectively kills target cells, it serves as a marker, or it provides a novel gene product not normally present in the target cell.

The RNA, DNA, or nucleotide analog which is used for trans-splicing is one whose expression product after trans-splicing results in cell death (for example, the expression of one molecule of diphtheria toxin subunit A will kill a human cell). In another embodiment, the expression product is secreted by the cell. In a further embodiment, the therapeutic RNA itself performs a desired function in the cell.

BRIEF DESCRIPTION OF THE DRAWINGS

FIGS. 1A, 1B, and 1C show the structure of Pre-Therapeutic Molecules of the invention.
These structures have 5 main features:
1) Target Binding Region:
One or two binding domains of at least 15 to 30 (up to several hundred) nucleotides which are complementary to and in anti-sense orientation to the targeted region of the selected pre-mRNA (a second target binding region could be located at the 3' end of the molecule). Other binding domains can be incorporated into the PTM. The binding domains can be enhanced with features such as the ability to cover or block sites required to splice downstream exons in the target mRNA, such as the branch point adenosine, spliceosomal binding sites, the polypyrimidine tract, or splice sites.
2) Spacer Region:
A spacer region to separate the therapeutic RNA splice site from the target binding domain. The spacer region can have features such as stop codons which would block any translation of an unspliced therapeutic RNA, and sequences that enhance splicing to target.

Figure 3A:
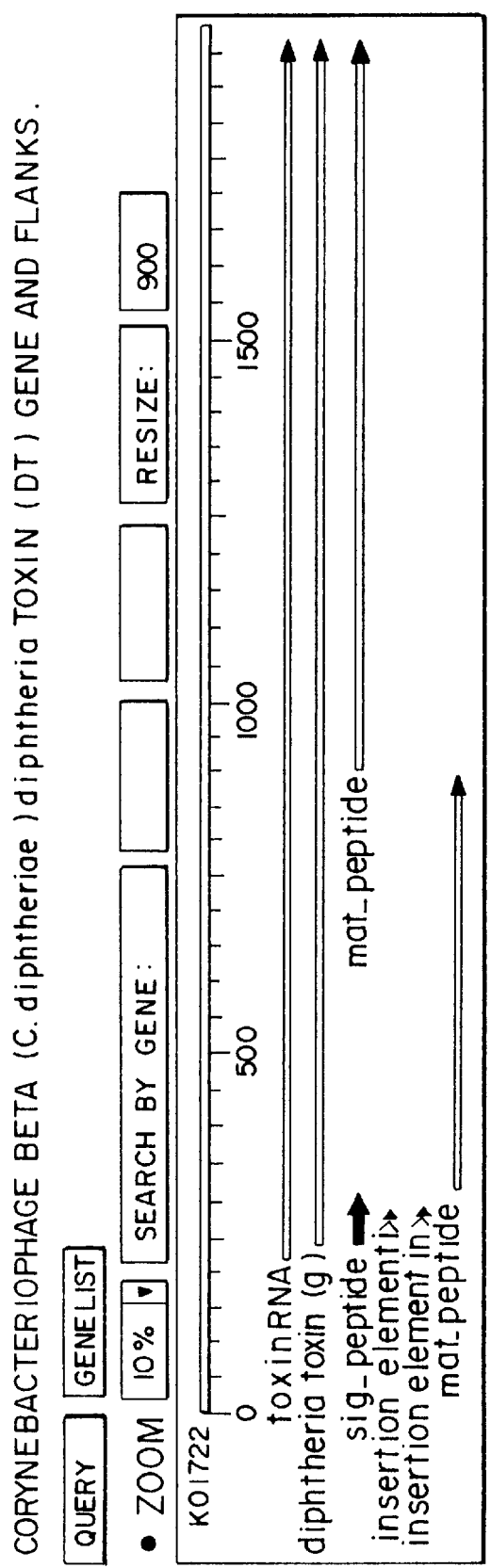

A "safety" for the pre-therapeutic molecule (PTM) may be incorporated into the spacer, binding domain, or elsewhere in the PTM (FIG. 1-B). This is a region of the PTM which covers elements of the 3' and/or 5' splice site of the PTM by relatively weak complementarity, preventing non-specific trans-splicing. Upon hybridization of the binding/targeting portion(s) of the PTM, the 3' splice site is uncovered and becomes fully active (See FIG. 1-C ).

The "safety" consists of one or more complementary stretches of cis-sequence (or could be a second, separate, strand of nucleic acid) which weakly binds to one or both sides of the PTM branch point, pyrimidine tract, and/or 3' splice site (splicing elements), or could bind to parts of the splicing elements themselves. This "safety" binding would prevent the splicing elements from being active (i.e. block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).
3) 3' and/or 5' SPLICE SITE:
This includes a branch point, pyrimidine tract and a 3' splice site.
4) Therapeutic Gene:
One or more therapeutic genes, such as diphtheria toxin, which is (are) to be spliced into the target mRNA and may be subsequently expressed, producing a therapeutic effect, such as cell death (A therapeutic gene can be one that gives a function of clinical usefulness, for example, restoring a missing function, acting as a marker, or killing unwanted cells).
5) Sequences Which Modulate Splicing and Translation:
There can be additional features added to the molecule after (or before) the toxin gene, such as polyadenylation signals or 5' splice sequences to enhance splicing, additional binding regions, "safety"-self complementary regions, additional splice sites, or protective groups to modulate the stability of the molecule (prevent degradation).

FIG. 2 shows the binding of the Pre-Therapeutic RNA and Trans-Splicing

2a) The cis-splicing product of A-B pre-mRNA into A-B mRNA, which is the normal pathway for the cell to subsequently express A-B protein.

2b) A pre-th-RNA molecule bound to an A-B pre-mRNA by complementary base pairing. In this example, the binding region blocks the cis-branch point adenosine and the 5' overhang may partially interfere with the cis-pyrimidine tract. This disrupts cis-splicing of exon B and presents the pre-th-RNA toxin gene as a candidate for trans-splicing to exon A.

2c) A trans-spliced product of A-B pre-mRNA and a pre-th-RNA. Exon A is linked to a toxin gene, which can now be expressed in a fully functional heterologous therapeutic RNA molecule (th-mRNA). Translation of this mRNA will cause the expressing cell to die.

FIG. 3 shows the map and sequence of Diphtheria toxin. The coding region for subunit A is from nucleotides 312–890.

FIG. 4 shows the construction of the pre-therapeutic molecules of the invention.

FIG. 5 shows the map and sequence of beta HCG.

FIGS. 6 A and B show the results of the trans-splicing reaction. FIG. 6A shows an agarose gel of the RT-PCR products and FIG. 6B shows the nucleotide sequence of the trans-spliced product.

FIG. 7 shows the results of the transfection toxicity assays of example 5.

DETAILED DESCRIPTION OF THE INVENTION

As indicated above, the present invention relates to the use of targeted pre-messenger RNA (pre-mRNA) trans-splicing as a means of producing a therapeutic molecule in the cell. The therapeutic molecule may itself provide a desired function, or may produce a gene product in the specific cell type. The gene products can be any gene, including genes having clinical usefulness, for example, therapeutic or marker genes, and toxins. In one embodiment of the invention, the gene delivered is a toxin gene, whereby the expression of one molecule is lethal to the cell containing the targeted pre-mRNA.

In one embodiment, the invention is directed to a method of creating a specific mRNA to cause the expression of a therapeutic toxin gene within the selected cell population, thereby destroying those specific cells. The target cells may include, but are not limited to those infected with viral or other infectious agents, benign or malignant neoplasms, or components of the immune system which are involved in autoimmune disease or tissue rejection. Specificity is achieved by modification of the binding domain of the PTM to bind to the target.

The steps comprising one embodiment of the method of the present invention are:

i) delivering to the nucleus of cells a precursor molecule, which may be of any form used by one skilled in the art, a therapeutic RNA molecule (or a DNA vector which may be transcribed into RNA or a synthetic analog) which precursor therapeutic RNA (pre-thRNA) contains a binding region which may bind through different mechanisms to the target pre-mRNA, a splice site, a therapeutic gene, and may contain polyadenylation signals, enhancers, or other modulating sequence elements [See FIG. 1, part A, B, and C];

ii) trans-splicing of the precursor therapeutic RNA molecule with a targeted pre-mRNA to create a therapeutic translatable mRNA [See FIG. 2*b*]; and iii) expression (translation) of the trans-spliced therapeutic mRNA within the target cell(s) [See FIG. 2*c*].

The target cells can be any cells that are known to express a unique population of pre-mRNAs, which pre-mRNAs can be used as substrate for the trans-splicing reaction. the unique population can be 1 unique type of RNA or several which, as a group, are not expressed together in any other cell type. The precursor therapeutic RNA will contain binding regions specific for the targeted pre-mRNA.

The pre-therapeutic molecule can be administered to cells by any delivery procedure, for example, virally mediated, electroporation, micro injection, calcium phosphate mediated transfection, liposomes, cytofectins, or directly. The pre-therapeutic molecule will be administered in amounts which are effective to produce the desired amount of the therapeutic molecule itself. The exact amount administered will vary depending upon the details of the delivery system. The effective amount may also vary depending upon whether the therapeutic molecule provides a missing function (such as in therapy of genetic disease), cell death (such as in therapy of cancer), or cell regulation (which may be used with different types of diseases). The effective amount may range from 0.001 pico g, or even less, to 1.0 g nucleic acid/kg body weight of the patient.

A therapeutic molecule can be one that provides some function of clinical usefulness, for example, restoring a missing function, acting as a marker, or killing unwanted cells.

In one embodiment, the pre-therapeutic RNA molecule is a non-translatable single-stranded RNA with four main features: 1) One or two binding domains of at least 15 to 30 nucleotides (and up to several hundred nucleotides or more) which are complementary to and in anti-sense orientation to the targeted region of the unique pre-mRNA. This confers the specificity of the binding and anchors the pre-therapeutic RNA closely in space so that the spliceosomal processing machinery of the nucleus can trans-splice it into the target pre-mRNA. The binding domains can be enhanced with features such as the ability to cover or block sites required to cis-splice downstream exons in the target pre-mRNA, such as the branch point adenosine, spliceosomal binding sites, the polypyrimidine tract, or authentic 3' or 5' splice sites. 2) A spacer region to line up the pre-therapeutic RNA splice site with the target. The spacer region can have features such as stop codons which would block any translation of an unspliced pre-therapeutic RNA, and sequences that enhance splicing to the target. The spacer is also serves to separate binding domain from splice site (and may contain a "safety"domain) 3) A 3' splice site. 4) One or more therapeutic genes, such as diphtheria toxin, which is (are) to be spliced into the target mRNA and subsequently expressed, producing a therapeutic effect, such as cell death, which is desirable when treating a malignancy. There can be additional features added as needed to the molecule after the toxin gene (open reading frame), such as polyadenylation signals or 5' splice sequences to enhance splicing and the steps leading to translation and expression. In the embodiment of the invention wherein the spliced RNA is itself the therapeutic molecule, there may be no therapeutic gene, but rather RNA with the desired effect. Trans-splicing may be mediated by any known mechanism (Group I, Group II, or spliceosome).

The methods of the present invention have enormous clinical application in the treatment of cancer, HIV/AIDS and other serious viral infections, autoimmune disorders, and other pathological conditions in which the alteration or elimination of a specific cell type would be beneficial. Examples of this include benign prostate hypertrophy and other pre-malignant conditions. Additionally, the method may also be used to treat inherited genetic disorders, such as Gaucher disease, where expression of a small amount of the missing or mutant gene product produces a normal phenotype.

In another embodiment, the PTM is a non-translatable single-stranded RNA with the features as listed above: 1) One or two binding domains; 2) Spacer region; 3) A 5' splice site, and 4) One or more therapeutic genes, and there can be additional sequences which confer additional features (as mentioned in the other examples). Trans-splicing may be mediated by any known mechanism, such as group I, group II, or spliceosome.

Maximizing trans-splicing

1. Pre-th-RNAs are constructed to complement and bind 5' and 3' from the BPA, and may or may not include the branch point adenosine (block it). This allows location of optimal anti-sense binding domain.

2. PTMs are made with and without the branch point adenosine in the pre-thRNA to determine if the inclusion of the BPA leads to non-selective splicing (into non-targeted mRNA's).

3. PTMs are made with and without stop codons or other elements in the region between the binding domain and the splice site, to determine is such elements absolutely prevent unspliced pre-thRNA expression.

4. PTMs are made with and without strong polyadenylation signal or downstream enhancer or 5' splice sequences downstream of the toxin gene, to determine if these elements promote trans-splicing.

5. PTMs are made with and without a second anti-sense binding domain downstream from the toxin gene to determine if such an element promotes binding to the 3' target exon and promotes extension to block the authentic cis-3' splice site (U5 and/or U1 binding sites). PTMs may also be made to require a second trans-splice for expression of the trans-spliced product.

Figure 5A:
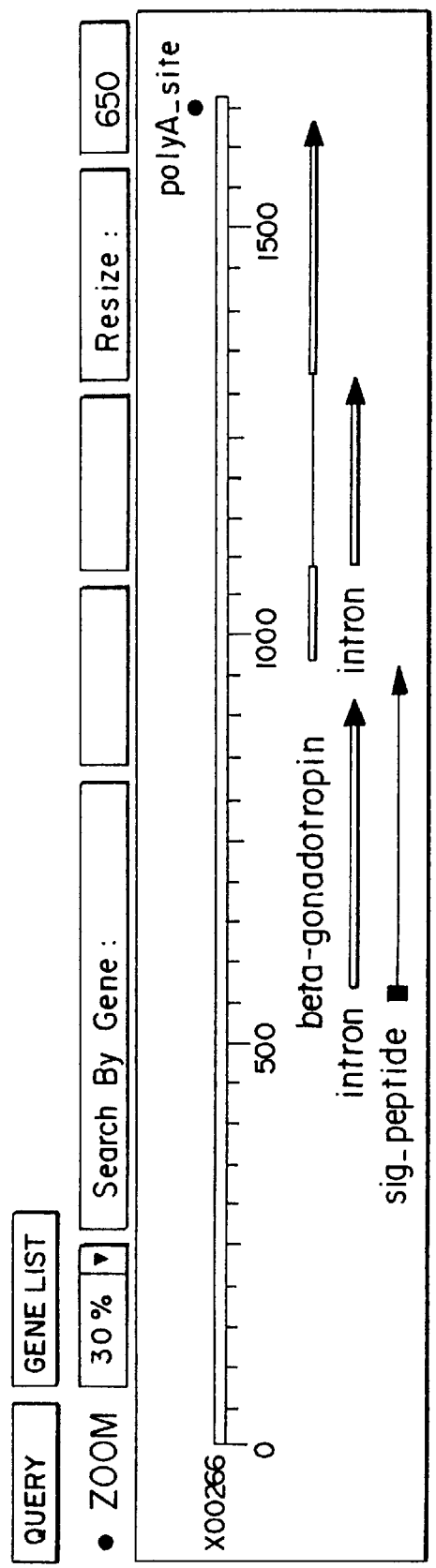

6. Further elements such as a 3' hairpin structure, circularized RNA, nucleotide base modification, or synthetic analog) are incorporated into constructs to promote or facilitate nuclear localization and spliceosomal incorporation, and intra-cellular stability.

7. The final therapeutic construct may have to be delivered from the external cell membrane and transit into the nucleus to be incorporated into the spliceosome of the targeted pre-mRNA, or they may be produced by the cell itself from a precursor molecule (DNA vector, RNA virus, etc.).

Delivery systems

The present invention can use any known delivery system developed for other gene treatment or anti-sense methods. The pre-therapeutic RNA must be made, packaged, and tested for cellular incorporation. Chemical synthesis of the full length pre-th-RNA is not currently practical, as chemical synthesis is limited to approximately 100 nucleotides, but could be possible. Full length pre-th-RNA is transcribed from PCR amplified templates (using high fidelity enzymes) or cloned DNA with an appropriate promoter incorporated. There are also RNA amplification methods such as Q-β amplification which can be utilized. The spliced th-RNA is purified and tested by sequencing or by ability to trans-splice target and produce toxin or marker in an in vitro system.

Liposomes, electroporation, and cytofections are methods of directly introducing RNA into cells. They are widely used in anti-sense RNA delivery protocols. Naked or packaged DNA is another possible means of delivery. Viral delivery systems may also be used; although they are more expensive to grow and manipulate, and may not be readily acceptable to the public. Viral vectors with transient expression, such as adenovirus and adeno-associated virus, which do not integrate into the genome may be less problematic. Nucleic acid polymers can also be delivered by attaching them to the empty shells of replication incompetent viruses. Cook, D. R. et al. Cancer Biother. 9(2), 131–141 (1994).

EXAMPLE 1

Selection of Therapeutic Gene

A therapeutic gene is any gene that provides some novel function including clinical usefulness, for example, restoring a missing function, acting as a marker, or killing unwanted cells. Genes for restoring missing functions can be genes encoding gene products missing or altered in known genetic diseases. Marker genes can be genes which cause the expression of specific heterologous proteins or peptides which may be used to identify or image cells. Genes for killing cells may be simple toxins or other genes which provide some function which enhances the susceptibility of the cells to subsequent treatments, such as radiation or chemotherapy.

Diphtheria toxin is a good example of a simple toxin. Native DT is made up of an A subunit and a B subunit. Diphtheria toxin subunit A contains the enzymatic toxin activity and will function if expressed or delivered into human cells. The B subunit is required for transmembrane movement into human cells. Subunit A can not enter intact cells by itself. Alone, subunit A has very low toxicity because it cannot cross the lipid bilayer of a cell membrane without the B subunit. Donovan, J. M. Simon and M. Montal, J. Biol. Chem 260, 8817–8823 (1985). The A subunit can exist in several conformations. The gene for Diphtheria toxin subunit A is just under 600 nt in length. Greenfield, L., M. Bjorn, G. Horn, D. Fong, G. Buck, R. Collier and D. Kaplan, Proc. Natl. Acad. Sci. USA 80 6853–6857 (1983) See FIG. 3. The DT-A peptide can be active with heterologous peptide sequences attached. Leckett, B. and R. J. Germinario, Cytotechnology 10(2), 125–136 (1992). As an additional safety measure, immunization against DT-A released into the extra-cellular environment may be possible. Barbieri, J. T., D. Armellini, J. Molkentin, and R. Rappuoli, Infect. Immun. 60(12) 5071–5077 (1992). There are a number of other known toxins which may be used in the present invention.

EXAMPLE 2

Construction of Pre-therapeutic Molecules

An in vitro model system is used to determine the parameters of the pre-therapeutic molecule and target mRNA for most efficient trans-splicing.

1. Demonstration of trans-splicing: experimental pre-thRNA molecules (PTMs) (See FIG. 4 and legend) containing complementary anti-sense binding domains to a pre-mRNA (which encompasses the branch point adenosine (BPA) of the target; thereby blocking the splicing of the cis downstream exon), various spacer regions containing an exposed BPA, a 3' splice site and a marker gene (diphtheria toxin subunit A-(DTA)) are added to an in vitro system containing all nuclear splicing components and a targeted pre-mRNA (beta HCG) See FIG. 5. Trans-splicing is demonstrated by reverse transcription polymerase chain reaction (RT-PCR) amplification using one primer complementary to the 5' exon 1 of beta HCG and a second (reverse) primer complementary to the marker gene (DTA). PCR products were sequenced to demonstrate the correct trans-splicing product of the upstream 5' exon and the marker gene.

Construction of PTM 1–8:

The experimental model target pre-mRNA, βHCG gene 6 (Fig. C), was restricted with Sac I and cloned into pBS- (Stratagene). This produced an 805 bp insert from nucleotide 460 to 1265 which includes the 5' untranslated region, initiation codon, exon 1, intron 1, exon 2, and most of intron 2. RNA transcripts are produced using a T7 polymerase transcription kit (Stratagene) from these pBS- clones.

For cell-free trans-splice experiments, the pre-therapeutic molecules were also constructed in pBS-. Diphtheria toxin subunit A (DTA) was PCR amplified using primers DT-1 (GGCGCTGCAGGGCGCTGATGATGTTGTTG) [SEQ ID NO. 13], which has a Pst I site at the 5' end and DT-2 (GGCGAAGCTTGGATCCGACACGATTTCCTGCACAGG) [SEQ ID NO: 14] which adds a Bam H1 and Hind III site to the 3' end of the PCR product. The PCR amplified DTA was digested with Hind III and Pst I and cloned into pBS-. The resulting pBS-DTA clone was cut with Eco RI and Pst I and the following oligonucleotides were ligated in, creating PTM+(PTM 1).

[SEQ ID NO: 15]
IN2-4: GGAAAAAAAAGAAGAGGTACCAGTTAGTACTCGAGT

CAGGCCCGGGTGAAGCATCTAGAG

[SEQ ID NO: 16]
IN3-1: AATTCTCTAGATGCTTCACCCGGGCCTGACTCGAGTAC

TAACTGGTACCTCTTCTTTTTTTTCCTGCA

These oligos contain restriction sites for Eco RI, Xba I, Xho I, Kpn I, and Pst I. IN2-4 is complementary to IN3-1. The 5' overhang of IN3-1 is used to ligate into the Eco RI site of the pBS- DTA clone. The 3' overhang of IN3-1 is used to ligate into the Pst I site of the pBS- DTA clone, forming PTM 1.

PTM—(PTM-3) is created by restriction digestion of PTM 1 with Eco RI and Xho I, gel electrophoretic removal of the small binding domain fragment, and ligating in the following two oligos:

[SEQ ID NO: 17]
IN-5: AATTCTCTAGATCAGGCCCGGGTGAAGCACTCGAG

[SEQ ID NO: 18]
IN-6: TGCTTCACCCGGGCCTGATCTAGAG

PTM+spacer (PTM 2) was produced by cutting PTM 1 with Xho I and ligating in the following oligos. Clones having spacer B in the sense direction from the T7 promoter of pBS- were chosen as PTM 2.

Spacer A: TCGAGCAACGTTATAATAATGTTC [SEQ ID NO: 19]

Spacer B: TCGAGAACATTATTATAACGTTGC [SEQ ID NO: 20]

"No stick" PTM—with spacer (PTM 4) is created by restriction digestion of PTM 3 with Xba I and Xho I, and ligating the following oligos. Clones having spacer B in the sense direction from the T7 promoter of pBS- were chosen as PTM 4.

IN-7: CTAGACAACGTTATAATAATGTTC [SEQ ID NO: 21]

IN-8: TCGAGAACATTATTATAACGTTGT [SEQ ID NO: 22]

Spacer A: TCGAGCAACGTTATAATAATGTTC [SEQ ID NO: 19]

Spacer B: TCGAGAACATTATTATAACGTTGC [SEQ ID NO: 20]

CRM with spacer (PTM 8) was created by PCR amplification of a diphtheria toxin subunit A mutant, CRM 197 DTA (which has a mutation at amino acid 52, Gly to Glu, which eliminates toxin activity, Uchida et al., 1973, JBC 248, 3838–3844) using primers DT-1 and DT-2. The product was digested with Hind III and Pst I and cloned into Hind III and Pst I digested PTM 2, after agarose gel electrophoresis to remove the wild type toxin gene from PTM 2.

PTM+Py tract (−) AG (−) (PTM 5) mutant was created by digesting PTM 2 clone with Pst I and Mung Bean Nuclease and then ligating in delta AG-1 and delta AG-2 oligos. Delta AG-I has a unique Hpa I restriction site.

Delta AG-1: CCGAACTGGACGCGGTTAAC [SEQ ID NO: 23]

Delta AG-2: GTTAACCGCGTCCAGTTCGGGTAC {SEQ ID NO: 24]

PTM+Py tract (−) AG (−) with stop condons (PTM 6) was created by digesting PTM 2 with Pst I and Mung Bean Nuclease and then ligating in delta AG-3 and delta AG-4 oligos. Delta AG-3 contains three stop condons in frame "TGA, TAA, TAG" and has a unique Hpa I restriction site.

Delta AG:3 CCGTGATAATAGCGGTTAAC [SEQ ID NO: 25]

Delta AG-4: GTTAACCGCTATTATCACGGGTAC [SEQ ID NO: 26]

PTM+AG (−) (PTM 7) mutant was created by PCR amplification of the Diphtheria toxin subunit A of PTM 2 using primers Delta AG-5 (ACTGGTACCTCTTCTTTTTTTT CCTGCGGCGCTG) [SEQ ID NO: 27], in which the 3' splice acceptor AG was deleted, and DT-2 (GGCGAAGCTTGGATCCGACA CGATTTCCTGCACAGG) [SEQ ID NO: 28], which has a Hind III site at the 3' end. The product was digested with Kpn I and Hind III and cloned into Kpn I and Hind III digested PTM 2, after agarose gel electrophoresis to remove the wild type toxin gene from PTM 2.

For studies involving cells in tissue culture, cloned PTM variations were digested with Eco RI and Hind III, then ligated into Eco RI and Hind III digested pcDNA 3.1- (Invitrogen), which is a mammalian expression vector containing a transformation selection marker (G418). The sequences of the various PTMs were verified by DNA sequencing.

Figure 6A:
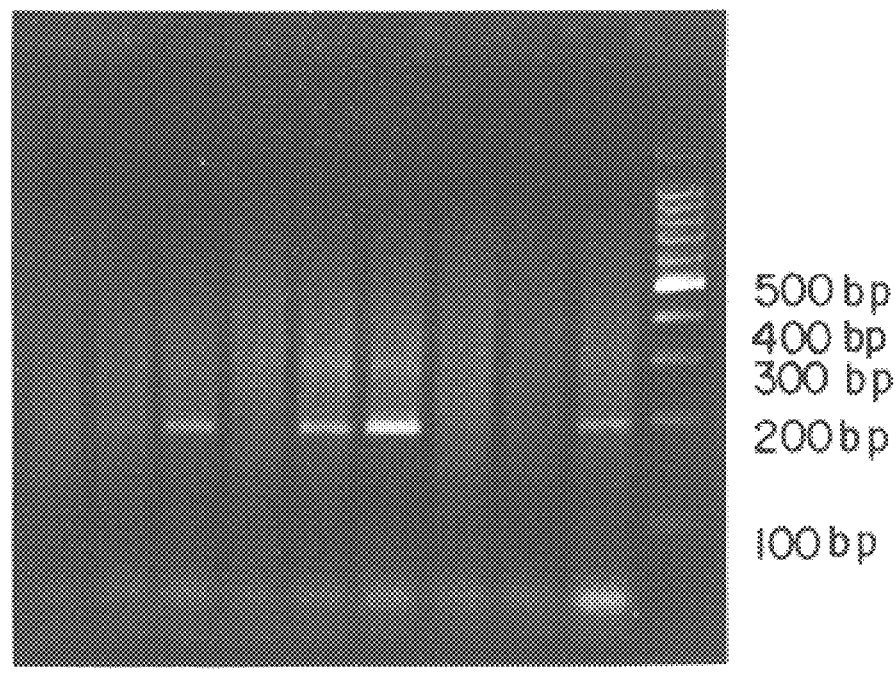

FIG. 6A shows an agarose gel of the RT-PCR products. The method for the in vitro trans-splicing and the RT-PCT analysis are as follows:

In vitro trans-splicing: 250 ng of gel purified βHCG pre-mRNA and 500 ng of the PTM RNA were annealed by heating to 98° C. in the presence of 40 mM KCl and 2 mM MgCl$_2$ and slowly cooled to 30° C. Splicing reactions were carried out by incubating 225 ng of the annealed RNA sample in a 25 µl reaction volume containing 1× splicing buffer (40 mM KCl, 2 mM MgCl$_2$, 5 mM creatinine phosphate and 1 mM ATP) and 8 µl of HeLa Splice nuclear extract (Promega) at 30° C. Aliquots were taken at the indicated time points and the reactions were stopped by adding an equal volume of high salt buffer (7 M urea, 0.5% SDS, 100 mM LiCl, 10 mM Tris-HCl, pH 7.5 and 10 mM EDTA). The RNA samples were extracted once with phenol:chloroform followed by chloroform, ethanol precipitated, washed with 70% ethanol and air dried.

RT-PCR Analysis: Reverse transcription (RT) coupled with PCR analysis were performed with a Perkin-Elmer thermal cycler using either a one enzyme protocol-EZ-RT Perkin-Elmer) or by using a two M-MLV reverse transcriptase (Gibco-BRL) and Taq DNA polymerase (Perkin-Elmer). Typical RT reaction volumes were 20 µl which contained 15 ng of spliced and trans-spliced RNA, 0.1 µg of a 3' specific primer which is complementary to the diphtheria toxin (nt 145–125 of DTA) portion of the trans-spliced RNA (DT-3,5'-CATCGTCATAATTTCCTTGTG), 5 mM MgCl$_2$, 1 mM of each dNTP 1× PCR buffer (50 mM KCl and 10 mM Tris-HCl, pH 8.3) and 10 U of reverse transcriptase. The RT reactions were carried at 42° C. for 15 min and for those RT using M-MLV, the enzyme was inactivated by heating to 95° C. for 5 min. The cDNA was then amplified by PCR using 0.1 µg of a 5' specific primer for the target component of the trans-spliced mRNA, βHCG RNA exon 1 (HCG-F, 5'-Biotin-ACCGGAATTCATGAAGCCAGGTACACCAGG, nt 514–534) and 2.5 U of Taq DNA polymerase in a 100 µl reaction volume. The temperature profile used in 35 cycles of amplification was denaturation at 94° C. for 30 s, annealing at 60° C. for 40 s and extension at 72° C. for 45 s followed by a final 7 min extension at 72° C. Reaction Products were analyzed on a 2% agarose gel. The expected product of trans-splicing is 207 bp.

FIG. 6-A shows that PTM+spacer (PTM 2) produced substantially more trans-spliced HCG/DTA product at 60 min than PTM 1 (PTM+) or PTM 4 (TB+spacer) and a five fold more trans-spliced HCG/DTA than PTM 1 or PTM 4 after a 90 min reaction in a HeLa nuclear extract splicing reaction. PTM 1 and PTM 4 produced roughly equivalent amounts of trans-spliced product after 90 minutes of incubation. This experiment demonstrates that an 18 nt binding region can significantly enhance the specificity of trans-splicing, when used in conjunction with a spacer region between the binding domain and the branch site. The lack of enhanced trans-splicing of PTM 1 over PTM 3 (data not shown) or PTM 4 is due to the proximity of the binding domain to the branch point in PTM 1, where binding to the target gene blocks the access of splicing factors to the adjacent branch point, as there is only 6 nt separating the sites. The small amount of non-targeted trans-splicing observed between beta HCG pre-mRNA and PTM 3 or PTM 4 was not unexpected, as PTM constructs 1–4 were produced using the yeast consensus branch site (UACUAAC), which has greater activity than the relatively weaker mammalian consensus, YNYURAC (where A is the site of branch formation, Y=pyrimidine, N=any nucleotide, and R=purine). Additionally, PTM constructs 1–4 contain a very strong pyrimidine tract. Together, this branch site-pyrimidine tract combination results PTMs with a high propensity to bind splicing factors, such as U2 AF and U2 snRNP, and to splice very efficiently. Moreover, the concentrations of target beta HCG pre-mRNA and pre-therapeutic molecules is supraphysiologic in this experiment, which enhances the probability of non-targeted (tethered) trans-splicing.

PTM 5 and PTM 6 have been designed to eliminate the pyrimidine tract and the 3' splice site in order to show that the joining of a PTM with the exon 1 of beta HCG is due to trans-splicing. PTM 7 was produced to remove only the 3' AG splice site. Patterson B and Guthrie C, Cell 64: 181–7 (1991). PTM 5–7 are being tested in transfected tissue culture experiments, as specificity within intact cells is more relevant for therapeutic application.

The experimental model intron is cloned into a section of the adenovirus 2 major late promoter Leader 1 and Leader 2 splicing unit, containing a 5' splice site, a branch point, pyrimidine tract, and a 3' splice site. This sequence is cloned into an expression vector, such as pcDNA3,1 (Invitrogen Corp.), with a T7 RNA promoter upstream, so that RNA of the splicing unit can be transcribed using T7 RNA polymerase (Stratagene). The nucleotide (DNA) sequence of one such insert is:

```
pcDNA11-T7 promoter 5'-
    GGGCGAATTCGAGCTCACTCTCTTCCGCATCGCTGTCTGCGA

GGTACCTGTTGGG/GTGAGTAGGATCCCTCTAAAAGCGGGCA
                 ↑
                 *
    TGACTTCTAGAGTAGTCCAGGGTTTCCGAGGGTTTCCGTCGA

CGATGTCATACTTATCCTGGGCCCTTTTTTTTCCACAG/CTC
           ↑                   #           ↑
           BPA                             **
    GCGCTGCAGGACAAACTCTTCGCGGTCTTTGCATGCAAGCTT (SEQ ID NO: 1)

3' Marker sequence
Key:
* = 5' Splice Site;
CATACT.. = target region for binding;
BPA = branch point adenosine;
# = Py tract;
** = 3'Splice Site
```

The 3' terminus of the model intron contains a marker sequence, such as the Sp6 promoter or expressible peptide selection markers, so that a properly spliced product is detectable by electrophoretic separation as a shorter mRNA sequence than an unspliced T7 transcript. The spliced product is also detectable by PCR amplification using primers to T7 and Sp6 sequences (or appropriate primer to the marker used).

Several regions of the pre-therapeutic RNA molecules are varied and tested for the ability to trans-splice specifically and determine the frequency of trans-splicing.

a) Binding domain—targeting the pyrimidine tract and branch point:

```
    CATACTTATCCTGGGCCCTTTT = TARGET Sequence of
the adenovirus 2 (SEQ ID NO:2) major late promoter
in 5' to 3' orientation
    3' - TTTTCCCGGGTCCTATTCATAC - 5' Target
sequence in reverse (SEQ ID NO:3) orientation
Model pre-thRNA molecule
    AAAAGGGCCCAGGATAAGTATGCACGGCGACTATTGATTCT
                                   ++++++++++++++++++++++

GAGAACTGTGTTATACTAACGGAACTTCCCTTTTTTTTCCACAG/
    ++++++++++++↑               #           **
                BPA
    AGCCAGCCAGAACTCGCCCCGGAAGACCCCGAGGATGTCGAG

CACCACCACCACCACCACTGAGATCCGGCTGCTAACAAAGCCCG
                                      ↑
                                      !
    AAAGGAAGCTGAGTTGGCTGCTGCCACGCTGAGCAATAACTAGC

ATAACCCCTTGGGGCCTCTAAACGGGTCTTGAGGGGTTTTTTG-3'

(SEQ ID NO:4)
Key:
AAAAGG.. = target region for binding;
+++++ = spacer region;
BPA = branch point adenosine;
# = Py tract;
** = 3' Splice Site;
ACCCAG... = HSV protein marker;
```

-continued

CACCAC... = histidine protein markers;
I = stop codon.

The inclusion of a histidine protein marker will allow for detection using metal chelation chromatography and HSV protein marker allows for detection using monoclonal antibodies. These reagents are available from Novagen, Inc.

b) Additional model pre-therapeutic RNA molecules are made which are similar to that above, with different complementary binding regions, shifted to hybridize either more 5' or 3' in the target molecule to ascertain the optimal region to target/block and to enhance the trans-splicing reaction. Other sequence elements which modulate splicing are added to enhance or diminish trans-splicing efficiency.

EXAMPLE 3

In Vitro Splicing Reaction

These DNA sequences were cloned into expression plasmids and hosts. Sequences were verified by Sanger dideoxy DNA sequencing. RNAs are made from plasmid DNA or PCR amplified templates and transcribed using T7 RNA polymerase. Either the target, or the pre-th-RNA may be synthesized in the presence of [SYMBOL 97 \f "Symbol"32P]UTP. Full length pre-mRNAs and targets are purified by gel electrophoresis. Jamison, S. F., A. Crow, and M. A. Garcia-Blanco, Mol. Cell Biol. 12, 4279–4287 (1992).

Nuclear extracts made using the procedure of Dignam, J. D. et al., (Nucl. Acids Res., 11, 1475–1489, 1983) were purchased from Promega. In vitro splicing assays were performed as in, Garcia-Blanco, M. A., S. F. Jamison, P. A. Sharp, (Genes and Dev., 3, 1874–1886, 1989). Splicing reactions are incubated for various times. Upon completion, the reaction products are separated by electrophoresis on polyacrylamide gels. Splicing complexes are electrophoresed on non-denaturing acrylamide gels and visualized by autoradiography. In vitro splicing products are analyzed on denaturing acrylamide gels. Jamison et al., Mol. Cell Biol. 12, 4279–4287 (1992).

Spliced products were analyzed by reverse transcription PCR (RT-PCR) in separate reactions using primers specific for either the native cis-spliced product, or for the hybrid trans-spliced product, with the 5' primer complementary to the target mRNA 5' exon, and the 3' primer complementary to the trans-spliced marker or therapeutic gene. The same 5' primer was used to detect the cis and trans-spliced product. There is increased trans-splicing conferred by the specificity of the binding domain. (See gel, FIG. 6A).

Spliced products may also be expressed in a cell free translation system, with the trans-spliced product detectable by Western blot and protein sequencing, under certain conditions, i.e. if the rate of trans-splicing is high enough to produce sufficient concentration of marker protein for detection.

Nucleotide sequences of RT-PCR amplified trans-spliced fragment. The RT-PCR amplified a 207 bp product, which was directly sequenced using DT-3 reverse primer, $\alpha$-$^{33}$PdATP and Sequenase kit (Amersham, Life Science), and the products were separated by gel electrophoresis. Arrows indicates the position of the junction of the trans-spliced product. (See FIG. 6-B).

EXAMPLE 4

Competitive In Vitro Splicing Reaction

This example is identical to example 3, except that it contains a mixture of pre-mRNA molecules, with only a limited amount of the targeted pre-mRNA. This allows demonstration of the trans-splicing reaction in the presence of a presumably preferred cis-splicing reaction. RT-PCR is used to determine the specificity of trans-splicing between the target pre-mRNA and the pre-thRNA in the presence of competing non-targeted pre-mRNAs. Additional RT-PCR amplifications using a primer to the marker sequence and primers specific to non-targeted pre-mRNA's are performed in order to detect possible random trans-splicing events.

EXAMPLE 5

Trans-splicing Reaction in Human Lung Cancer Cultured Cells

A cell culture model of a human lung cancer was used to demonstrate that therapeutic removal (killing) of target cells expressing a unique gene (pre-mRNA) is accomplished using the pre-therapeutic toxin molecules of the invention. Mixed cell experiments are used to show that only the target cells are eliminated. Successful pre-thRNA constructs identified during in vitro experiments were modified appropriately for use in the cell culture experiments. Experiments are currently underway to improve the specificity of cell killing, such as the addition of a "safety".

Cellular Disease Model: A cell culture model of human cancer was used to demonstrate that therapeutic removal (killing) of target cells expressing a unique gene (pre-mRNA) is accomplished using the pre-therapeutic molecules of the invention. In this system, various cancer cell lines, including a lung cancer line (H1299), a line derived from cervical cancer (HeLa S3), and several pancreatic cancer lines (C1469, C1997, H134 and C1682) were tested. All these cell lines have been found to express βHCG target molecules as determined by RT-PCR and immunostaining assays. Cells were plated at a density of 1×10$^5$ on 60 mm tissue culture plates and grown for a minimum of 24 hours. Transfection of CMV and PTM vector DNAs (4 µg/plate) was achieved using lipofectamine (Gibco-BRL) by standard procedure. On day 4, transfected cells were trypsinized and passed 1:10 into media containing G418 (500 µg/ml). Fresh media containing G418 was supplemented every 3–7 days. On day 18, colonies that remained after G418 selection were washed with PBS (Sigma), fixed in a 3:1 methanol/acetic acid solution for 10 min and air dried for 10 min. Then a 0.03% methylene blue solution was added for 10 min. to stain the colonies. Colonies were washed in PBS, air dried, and colonies of greater than 50 cells were counted. Results for the first experiments with H1299, a lung cancer cell line, and HeLa S3, derived from a cervical cancer are as follows:

| TRANSFECTION TOXICITY ASSAYS | | |
|---|---|---|
| CONDITION | Number of Colonies, Average, Plate A + B | Comment: |
| Cell Line: H1299 Experiment 1 | | |
| Mock (no DNA) | 0 | |
| PTM 8 | 91.0 | CRM mutant DTA, no toxin activity clone |
| pCMV control | 34.3 | Vector control for p53 clone |
| p53 in pCMV | 0 | Expressed p53 kills these cells, transformation + control |
| PTM4 | 4.7 | Non-binding PTM |
| PTM2 | 4.1 | Binding PTM |

-continued

TRANSFECTION TOXICITY ASSAYS

| CONDITION | Number of Colonies, Average, Plate A + B | Comment: |
|---|---|---|
| Cell Line; H1299 Experiment 2 | | |
| PTM 8 | 80.8 | CRM mutant DTA |
| pc3.1-vector | 115.3 | Vector control for PTM expression clones |
| PTM 4 | 1.0 | Non-binding PTM |
| PTM 2 | 2.0 | Binding PTM |
| Cell Line: HeLa S3 Experiment 1 | | |
| Mock (no DNA) | 88 | These plates were likely pCMV, but mislabeled Mock CRM mutant DTA |
| PTM 8 | 89 | CRM mutant DTA |
| pCMV control | 0 | These plates were likely Mock, but mislabeled pCMV |
| p53 in pCMV | 0 | Expressed p53 kills these cells, transformation + control |
| PTM 4 | 1.0 | Non-binding PTM |
| PTM 2 | 3.1 | Binding PTM |

Transfection of H1299 and HeLa S3 Cells: H1299 lung tumor cells and HeLa S3 derived cervical cancer cells were grown in RPMI media supplemented with 10% fetal calf serum at 37° C. in a 5% $CO_2$ incubator. Transfection was performed using lipofectamine (Gibco-BRL) according to standard procedure of the manufacturer. H1299 and HeLa S3 cells were plated at a density of $1\times10^5$ on 60 mm dishes and grown at least for 24 hr. Cells were either mock transfected, no DNA added, or transfected with 4 μg of the following vector DNAs: pc3.1-PTM 2 (PTM 2 cloned into pc3.1-), pc3.1-PTM 4 (PTM 4 cloned into pc3.1-), pc3.1-PTM 8 (identical to pc3.1-PTM 2, except for a point mutation which produces a Gly to Glu mutation at amino acid position 52 of DTA, eliminating all toxin enzymatic activity), pcDNA 3.1 (vector control), pCMV p53 (p53 cloned into pCMV), and pCMV (vector control). On day 4, transfected cells were trypsinized and passed 1:10 into media containing G418 (500 μg/ml). The medium was changed every 3 to 7 days and selection continued for at least 2 weeks. On day 18, colonies that remained after G418 selection were washed with PBS (Sigma), fixed in methanol/acetic acid solution (3:1) for 10 min and air dried for 10 min. Then 0.03% methylene blue was added for 10 min to stain the colonies, they were then washed once Preliminary studies suggest that the 1st generation of PTMs may have a high rate of non-targeted (promiscuous) trans-splicing. This was not an unexpected result, as the 1st generation PTMs were designed to maximize splicing efficiency. Several modifications to improve specificity are being tried. These include:

1. The addition of a "safety" to cover some or all of the splicing elements of the PTM
2. Changing the sequences of the branch point and pyrimidine tract so that they are less efficient splicing elements
3. Altering the 3' end of the PTM, so that it does not contain any polyadenylation signal, but is able to undergo a second trans-splicing reaction, acting as the 5' donor splice site to the 3' splice site of the terminal exon of a beta HCG, thereby acquiring the polyadenylation signal needed for export to the cytoplasm and translation of the therapeutic chimeric protein.
4. Cloning the PTM into an inducable expression vector, where the amount of PTM transcribed can be regulated (perhaps trans-splicing is a common event).

EXAMPLE 6

Trans-Splicing Reaction in Human Cervical Carcinoma Cell Lines

The constructs are optimized for stability and ability to bind to a specific site and to assure that the pre-therapeutic molecule can be produced in, transported to, and/or delivered to the cellular site where splicing is desired. Preliminary studies were done using eukaryotic expression plasmids, which produce the pre-th-RNA construct within the nucleus, so specific binding, targeted trans-splicing and stability are the design goals for the initial pre-therapeutic molecules. A vector containing an inducible promoter may be used for convenience or to regulate the concentration of PTMs in the cell. Induction of the pre-therapeutic RNA is attained by the introduction into the media of a simple non-toxic chemical. For example, IPTG induces transcription of insert in pOP13 CAT (Stratagene). An additional second selectable marker, such as neomycin resistance, may also be incorporated; with such a marker, only cells which have taken up the vector will survive under selective growth conditions.

Other possible disease models with unique gene targets include: a human cervical carcinoma cell line expressing papilloma virus E6 or E7 protein, a prostate cancer cell line expressing prostate specific antigen, a human hepatic carcinoma cell line expressing CEA protein, or other lines expressing a tissue specific gene product (pancreas, liver, breast, colon, melanoma) or producing a malignancy associated protein, such as HCG (human chorionic gonadotropin), leukemia with bcrabl fusion gene product t(9a34;22q11), or other chromosomal translocation fusion genes.

A papilloma virus model system may be tested next. The treatment of cervical dysplasia and cancer are major clinical problems. This model offers the ability to demonstrate effectiveness against both a cancer and a viral infection. Women infected with serotypes 16 or 18 of papilloma virus expressing the E6 and E7 genes are at high risk to develop cervical cancers.

The initial work is done on a cell line which is transfected with a selectable expression plasmid (such as ability to grow in the presence of a normally toxic antibiotic, such as hygromycin resistance conferred by plasmid pREP4 (available from Stratagene) into which is cloned a contiguous region of a papilloma virus type 18 containing E6 and E7 and a splicing region containing a 5' splice site, a BP, pyrimidine tract and 3' splice site to target (plasmid 1).

Demonstration of trans-splicing: The above cell line is transfected with a second expression plasmid (plasmid 2), with a different selectable marker, such as G418 (neomycin) resistance as provided by pcDNA I Neo (Stratagene), and an expression cassette encoding a pre-therapeutic RNA made by the expression plasmid 1. As before, the pre-thRNA molecule has an anti-sense binding domain which may block the BPA of the target pre-mRNA, a spacer region, a branch point, pyrimidine tract, a 3' splice site and a marker or toxin gene and splice modulating sequences. In the case that the trans-spliced gene is a toxin gene, these cells would not be expected to survive for very long. Trans-splicing is demonstrated by expression of a marker protein (in the case of a marker gene) or a toxin. The toxin may be detectable by an antibody, or the presence of the hybrid mRNA may be detected by RT-PCR.

Transfected cells were assayed by growth inhibition assays according to the method of El-Deiry, et al (Cell 75, 817–825, 1993). Cells were transfected with an expression plasmid. Colonies are selected on the basis of growth in the presence of G418. Cells were expanded, split into three groups, and transfected with plasmids containing: a) a target binding pre-thRNA with an authentic toxin gene (PTM2), b) a pre-thRNA with a mutated or anti-sense oriented toxin gene (PTM8), c) no insert (pc3.1 vector control) or d) a non-target binding (non-homologous) PTM, PTM4. Growth inhibition is measured as a reduction in the number of antibiotic resistant colonies generated. CMV (cytomegalovirus) based vectors allow constitutive high level expression of the transfected gene in target cells. The results are shown above. A reverse experiment can be performed beginning with cells transfected with plasmid 2 first and intact or mutated target plasmids (plasmid 1).

Brief description of a double transfection experiment: Cells are plated in petri dishes and transfected with a fixed amount of plasmid 1 (target with hygromycin resistance), usually 2 μg of DNA, and with plasmid 2 (containing pre-th-RNA and G418 resistance) at various concentrations. Selection for colonies resistant by incubation in G418 and/or hygromycin for 2–3 weeks. Colonies will be stained with methylene blue and counted.

Assay results—Theoretical:
1. Control (no transfection)—No colonies
2. Control (2 μg plasmid 1)—200–500 colonies
3. Control (2 μg plasmid 2 without toxin gene [either deleted or mutated], and 2 μg plasmidal)—200500 colonies
4. 2 μg plasmid 1 and 2 μg plasmid 2—20–50 colonies
5. 2 μg plasmid 1 and 20 μg plasmid 2—2–5 colonies Conclusion: Plasmid 2, containing functional toxin gene in pre-thRNA molecule, inhibits the growth of these cells.

Brief description of an alternate transfection experiment: Cells are plated in petri dishes and transfected with a fixed amount of plasmid 2 (containing pre-th-RNA and G418 resistance) at various concentrations. Selection for colonies resistant by incubation in G418 and/or hygromycin for 2–3 weeks. Colonies will be stained with methylene blue and counted.

Assay results—Theoretical:
1. Control (no transfection)—No colonies
2. Control (4 μg plasmid 1)—200–500 colonies
3. Control (4 μg plasmid 2 without toxin gene [either deleted or mutated], and 4 μg plasmidal)—200500 colonies
4. 4 μg plasmid 1 and 4 μg plasmid 2—20–50 colonies
5. 4 μg plasmid 1 and 20 μg plasmid 2—2–5 colonies Conclusion: Plasmid 2, containing functional toxin gene in pre-thRNA molecule, inhibits the growth of these cells.

Experimental controls are performed to demonstrate that cell growth inhibition is due to expression of the toxin and not due to the production of a cytokine, such as interferon, that would be expected to occur when double stranded RNA is present within cells. In these experiments, the binding domain is changed so that it no longer binds, or the toxin gene is mutated so that it is not expressible by the insertion of a frameshift nonsense point mutation, or insertion of the toxin gene in an anti-sense orientation, but the rest of the construct will be unaltered. Cells transfected with plasmid 1 and plasmid 2 with no binding domain or an inexpressible toxin gene should grow as well as cells containing no pre-thRNA construct.

Mixed cell experiments are done. These include studies where cells lacking plasmid 1 are transfected with plasmid 2 along with cells containing plasmid 1. The final population should be able to grow well in the presence of G418 (the resistance conferred by plasmid 2), but should not grow in the presence of selective agent 1 (the cells containing both plasmids should be eliminated by the trans-spliced toxin). Additional mixed cultures may be done to demonstrate that the expression of toxin within adjacent cells does not affect the survival of non-targeted cells.

EXAMPLE 7

Animal Experiments

1st Phase (mice)

Transformed cells with inducible pre-thRNA plasmids are administered to mice. These cells will be developed in the cell culture model described above, and one therefore obtains diseased animals with an inducible promoter in front of the trans-spliceable construct. The vector is then induced and the disease cells are killed by the expression of the toxin and the animal should remain healthy. This latter point is important to show that the induction of the toxin gene does not have a generalized adverse effect. Some of the disease cells are also examined soon after induction to search with antibodies for evidence of toxin gene expression and also to perform reverse transcription PCR to demonstrate that trans-splicing occurred. The animals are followed for long term survival and possible toxicity. Athymic mice can be used to grow human cells. Alternatively the PTMs can be administered by electroporation or liposomes.

2nd Phase—Therapeutic Concept Demonstration

In this phase animals with un-transformed disease cells are used (preferably human cells in athymic mice). Human pancreatic or lung cancer cells expressing beta HCG may be used with the PTMs developed for the experiments previously listed. Human cervical cancer cells containing the target region of the papilloma virus type 18 used in the cell model above can be used. Athymic mice with human pancreatic cancer or cervical cancer tumors are injected or electroporated with the deliverable form of the pre-therapeutic RNA construct. Control animals receive pre-th-RNA with expression incompetent toxin genes or sham (non-target binding) pre-th-RNAs. The animals are examined as above for long term survival and toxicity.

We claim:

1. A cell comprising a nucleic acid molecule wherein said nucleic acid molecule comprises:
   a) one or more target binding domains that target binding of the nucleic acid molecule to a target pre-mRNA expressed within the cell;
   b) a 3' splice region comprising a branch point, a pyrimidine tract and a 3' splice acceptor site;
   c) a spacer region that separates the 3' splice region from the target binding domain; and
   d) a nucleotide sequence to be trans-spliced to the target pre-mRNA;
   wherein said nucleic acid molecule is recognized by nuclear splicing components within the cell.

2. The cell of claim 1 wherein the nucleic acid molecule further comprises a 5' donor site.

3. The cell of claim 1 wherein the nucleic acid molecule further comprises a safety nucleotide sequence comprising one or more complementary sequences that bind to one or more sides of the 3' splice region.

4. The cell of claim 1 wherein the binding of the nucleic acid molecule to the target pre-mRNA is mediated by complementary, triple helix formation or protein-nucleic acid interaction.

5. The cell of claim 1 wherein the nucleic acid molecule further comprises sequences encoding a translatable protein product.

6. The cell of claim 1 wherein the nucleic acid molecule further comprises a nucleotide sequence containing a translational stop codon.

7. The cell of claim 5 wherein the translatable protein product is a toxin.

8. The cell of claim 5 wherein the toxin is subunit A of Diptheria toxin.

9. A cell comprising a nucleic acid molecule wherein said nucleic acid molecule comprises:
   a) one or more target binding domains that target binding of the nucleic acid molecule to a target pre-mRNA expressed within the cell;
   b) a 5' splice site;
   c) a spacer region that separates the 5' splice site from the target binding domain; and
   d) a nucleotide sequence to be trans-spliced to the target pre-mRNA;
   wherein said nucleic acid molecule is recognized by nuclear splicing components within the cell.

10. A cell comprising a recombinant vector wherein said vector expresses a nucleic acid molecule comprising:
    a) one or more target binding domains that target binding of the nucleic acid molecule to a target pre-mRNA expressed within the cell;
    b) a 3' splice region comprising a branch point, a pyrimidine tract and a 3' splice acceptor site;
    c) a spacer region that separates the 3' splice region from the target binding domain; and
    d) a nucleotide sequence to be trans-spliced to the target pre-mRNA;
    wherein said nucleic acid molecule is recognized by nuclear splicing components within the cell.

11. The cell of claim 10 wherein the nucleic acid molecule further comprises a 5' donor site.

12. A cell comprising a recombinant vector wherein said vector expresses a nucleic acid molecule comprising:
    a) one or more target binding domains that target binding of the nucleic acid molecule to a target pre-mRNA expressed within the cell;
    b) a 5' splice site;
    c) a spacer region that separates the 5' splice site from the target binding domain, and
    d) a nucleotide sequence to be trans-spliced to the target pre-mRNA;
    wherein said nucleic acid molecule is recognized by nuclear splicing components within the cell.

13. A method of producing a chimeric RNA molecule in a cell comprising:
    contacting a target pre-mRNA expressed in the cell with a nucleic acid molecule recognized by nuclear splicing components wherein said nucleic acid molecule comprises:
      a) one or more target binding domains that target binding of the nucleic acid molecule to a target pre-mRNA expressed within the cell;
      b) a 3' splice region comprising a branch point, a pyrimidine tract and a 3' splice acceptor site;
      c) a spacer region that separates the 3' splice region from the target binding domain; and
      d) a nucleotide sequence to be trans-spliced to the target pre-mRNA;
    under conditions in which a portion of the nucleic acid molecule is trans-spliced to a portion of the target pre-mRNA to form a chimeric RNA within the cell.

14. A method of claim 13 wherein the nucleic acid molecule further comprises a 5" donor site.

15. The method of claim 13, wherein the chimeric RNA molecule comprises sequences encoding a translatable protein.

16. The method of claim 13, wherein the chimeric RNA molecule comprises sequences encoding a toxin.

17. The method of claim 13, wherein the chimeric RNA molecule comprises sequences encoding Diptheria toxin.

18. A method of producing a chimeric RNA molecule in a cell comprising:
    contacting a target pre-mRNA expressed within the cell with a nucleic acid molecule recognized by nuclear splicing components wherein said nucleic acid molecule comprises:
      a) one or more target binding domains that target binding of the nucleic acid molecule to a target pre-mRNA expressed within the cell;
      b) a 5' splice site;
      c) a spacer region that separates the 5' splice site from the target binding domain; and d) a nucleotide sequence to be trans-spliced to the target pre-mRNA;

wherein said nucleic acid molecule is recognized by nuclear splicing components within the cell.

19. A nucleic acid molecule comprising:
   a) one or more target binding domains that target binding of the nucleic acid molecule to a target pre-mRNA expressed within the cell;
   b) a 3' splice region comprising a branch point, a pyrimidine tract and a 3' splice acceptor site;
   c) a spacer region that separates the 3' splice region from the target binding domain;
   d) a safety sequence comprising one or more complementary sequences that bind to one or both sides of the 3' splice site; and
   e) a nucleotide sequence to be trans-spliced to the target pre-mRNA;

wherein said nucleic acid molecule is recognized by nuclear splicing components within the cell.

20. A nucleic acid molecule comprising:
   a) one or more target binding domains that target binding of the nucleic acid molecule to a target pre-mRNA expressed within the cell;
   b) a 5' splice site;
   c) a spacer region that separates the 5' splice site from the target binding domain;
   d) a safety sequence comprising one or more complementary sequences that bind to one or both sides of the 5' splice site; and
   e) a nucleotide sequence to be trans-spliced to the target pre-mRNA;

wherein said nucleic acid molecule is recognized by nuclear splicing components within the cell.

21. The nucleic acid molecule of claim 19 or 20 wherein the nucleic acid molecule further comprises a 5' donor site.

22. The nucleic acid molecule of claim 21 wherein the binding of the nucleic acid molecule to the target pre-mRNA is mediated by complementary, triple helix formation, or protein-nucleic acid interaction.

23. The nucleic acid molecule of claim 21 wherein the nucleic acid molecule further comprises sequences encoding a translatable protein product.

24. The nucleic acid molecule of claim 21 wherein the nucleic acid molecule further comprises a nucleotide sequence containing a translational stop codon.

25. The nucleic acid molecule of claim 21 wherein the translatable protein product is a toxin.

26. The nucleic acid molecule of claim 21 wherein the toxin is subunit A of Diptheria toxin.

27. The nucleic acid molecule of claim 19 or 20 wherein the binding of the nucleic acid molecule to the target pre-mRNA is mediated by complementary, triple helix formation, or protein-nucleic acid interaction.

28. The nucleic acid molecule of claim 19 or 20 wherein the nucleic acid molecule further comprises sequences encoding a translatable protein product.

29. The nucleic acid molecule of claim 19 or 20 wherein the nucleic acid molecule further comprises a nucleotide sequence containing a translational stop codon.

30. The nucleic acid molecule of claim 19 or 20 wherein the translatable protein product is a toxin.

31. The nucleic acid molecule of claim 19 or 20 wherein the toxin is subunit A of Diptheria toxin.

32. A eukaryotic expression vector wherein said vector expresses a nucleic acid molecule comprising:
   a) one or more target binding domains that target binding of the nucleic acid molecule to a target pre-mRNA expressed within the cell;
   b) a 3' splice region comprising a branch point, a pyrimidine tact and a 3' splice acceptor site;
   c) a spacer region that separates the 3' splice region from the target binding domain; and
   d) a nucleotide sequence to be trans-spliced to the target pre-mRNA;

wherein said nucleic acid molecule is recognized by nuclear splicing components within the cell.

33. The vector of claim 32 wherein the nucleic acid molecule further comprises a 5' donor site.

34. A eukaryotic expression vector wherein said vector expresses a nucleic acid molecule comprising:
   a) one or more target binding domains that target binding of the nucleic acid molecule to a target pre-mRNA expressed within the cell;
   b) a 5' splice site;
   c) a spacer region that separates the 5' splice site from the target binding domain; and
   d) a nucleotide sequence to be trans-spliced to the target pre-mRNA;

wherein said nucleic acid molecule is recognized by nuclear splicing components within the cell.

* * * * *